(12) United States Patent
Nelson et al.

(10) Patent No.: US 8,287,539 B2
(45) Date of Patent: Oct. 16, 2012

(54) FRACTURE FIXATION DEVICE, TOOLS AND METHODS

(75) Inventors: Charles L. Nelson, Santa Rosa, CA (US); Trung Ho Pham, Santa Rosa, CA (US); Stephen R. McDaniel, San Rafael, CA (US); Heber Saravia, Santa Rosa, CA (US); Nathan Brown, Santa Rosa, CA (US); Thomas R. Hackett, Vail, CO (US); Lonnie Paulos, Pensacola, FL (US); Robert G. Coleman, Santa Rosa, CA (US)

(73) Assignee: Sonoma Orthopedic Products, Inc., Santa Rosa, CA (US)

( * ) Notice: Subject to any disclaimer, the term of this patent is extended or adjusted under 35 U.S.C. 154(b) by 498 days.

(21) Appl. No.: 12/482,388

(22) Filed: Jun. 10, 2009

(65) Prior Publication Data
US 2010/0094347 A1    Apr. 15, 2010

Related U.S. Application Data

(63) Continuation-in-part of application No. 11/383,269, filed on May 15, 2006, now Pat. No. 7,846,162, and a continuation-in-part of application No. 11/383,800, filed on May 17, 2006, now abandoned, application No. 12/482,388, which is a continuation-in-part of application No. 11/944,366, filed on Nov. 21, 2007, now Pat. No. 7,909,825.

(60) Provisional application No. 60/682,652, filed on May 18, 2005, provisional application No. 60/867,011, filed on Nov. 22, 2006, provisional application No. 60/866,976, filed on Nov. 22, 2006, provisional application No. 60/949,071, filed on Jul. 11, 2007, provisional application No. 61/060,440, filed on Jun. 10, 2008, provisional application No. 61/060,445, filed on Jun. 10, 2008, provisional application No. 61/060,450, filed on Jun. 10, 2008, provisional application No. 61/100,635, filed on Sep. 26, 2008, provisional application No. 61/100,652, filed on Sep. 26, 2008, provisional application No. 61/122,563, filed on Dec. 15, 2008, provisional application No. 61/138,920, filed on Dec. 18, 2008, provisional application No. 61/117,901, filed on Nov. 25, 2008.

(51) Int. Cl.
*A61B 17/58* (2006.01)

(52) U.S. Cl. .......................................... 606/62; 606/63

(58) Field of Classification Search .............. 606/62–68, 606/60; 411/21
See application file for complete search history.

(56) References Cited

U.S. PATENT DOCUMENTS 958,127 A    5/1910   Hufrud
(Continued)

FOREIGN PATENT DOCUMENTS

CA    2561552 A1    11/2005
(Continued)

OTHER PUBLICATIONS

Andermahr et al.; Anatomy of the clavicle and the intramedullary nailing of midclavicular fractures; Clinical Anatomy; vol. 20; pp. 48-56; 2007.

(Continued)

*Primary Examiner* — Jan Christopher Merene
(74) *Attorney, Agent, or Firm* — Knobbe Martens Olson & Bear, LLP

(57) ABSTRACT

A bone fixation device is provided with an elongate body having a longitudinal axis and having a first state in which at least a portion of the body is flexible and a second state in which the body is generally rigid, an actuateable gripper disposed at a distal location on the elongated body, and an actuator operably connected to the gripper to deploy the gripper from a retracted configuration to an expanded configuration. Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone.

26 Claims, 26 Drawing Sheets

U.S. PATENT DOCUMENTS

| | | |
|---|---|---|
| 1,169,635 A | 1/1916 | Grimes |
| 1,790,841 A | 2/1931 | Rosen |
| 2,502,267 A | 3/1950 | McPherson |
| 2,685,877 A | 8/1954 | Dobelle |
| 2,998,007 A | 8/1961 | Herzog |
| 3,118,444 A | 1/1964 | Serrato, Jr. |
| 3,626,935 A | 12/1971 | Pollock et al. |
| 3,710,789 A | 1/1973 | Ersek |
| 3,759,257 A | 9/1973 | Fischer et al. |
| 3,760,802 A | 9/1973 | Fischer et al. |
| 3,779,239 A | 12/1973 | Fischer et al. |
| 3,791,380 A | 2/1974 | Dawidowski |
| 3,846,846 A | 11/1974 | Fischer |
| 3,955,565 A | 5/1976 | Johnson, Jr. |
| 3,978,528 A | 9/1976 | Crep |
| 3,986,504 A | 10/1976 | Avila |
| 4,007,528 A | 2/1977 | Shea et al. |
| 4,011,602 A | 3/1977 | Rybicki et al. |
| 4,016,874 A | 4/1977 | Maffei et al. |
| 4,065,816 A | 1/1978 | Sawyer |
| 4,091,806 A | 5/1978 | Aginsky |
| 4,146,022 A | 3/1979 | Johnson et al. |
| 4,164,794 A | 8/1979 | Spector et al. |
| 4,190,044 A | 2/1980 | Wood |
| D255,048 S | 5/1980 | Miller |
| 4,204,531 A | 5/1980 | Aginsky |
| 4,227,518 A | 10/1980 | Aginsky |
| 4,236,512 A | 12/1980 | Aginsky |
| 4,237,875 A | 12/1980 | Termanini |
| 4,246,662 A | 1/1981 | Pastrick |
| 4,262,665 A | 4/1981 | Roalstad et al. |
| 4,275,717 A | 6/1981 | Bolesky |
| 4,293,962 A | 10/1981 | Fuson |
| 4,294,251 A | 10/1981 | Greenwald et al. |
| 4,312,336 A | 1/1982 | Danieletto et al. |
| 4,338,926 A | 7/1982 | Kummer et al. |
| 4,351,069 A | 9/1982 | Ballintyn et al. |
| 4,352,212 A | 10/1982 | Greene et al. |
| 4,353,358 A | 10/1982 | Emerson |
| 4,379,451 A | 4/1983 | Getscher |
| 4,409,974 A | 10/1983 | Freedland |
| 4,453,539 A | 6/1984 | Raftopoulos et al. |
| 4,457,301 A | 7/1984 | Walker |
| 4,462,394 A | 7/1984 | Jacobs |
| 4,467,794 A | 8/1984 | Maffei et al. |
| RE31,809 E | 1/1985 | Danieletto et al. |
| 4,492,226 A | 1/1985 | Belykh et al. |
| 4,503,847 A | 3/1985 | Mouradian |
| 4,519,100 A | 5/1985 | Wills et al. |
| 4,520,511 A | 6/1985 | Gianezio et al. |
| 4,522,200 A | 6/1985 | Stednitz |
| 4,552,136 A | 11/1985 | Kenna |
| 4,589,883 A | 5/1986 | Kenna |
| 4,590,930 A | 5/1986 | Kurth et al. |
| 4,604,997 A | 8/1986 | De Bastiani et al. |
| 4,621,627 A | 11/1986 | De Bastiani et al. |
| 4,622,959 A | 11/1986 | Marcus |
| 4,628,920 A | 12/1986 | Mathys, Jr. et al. |
| 4,632,101 A | 12/1986 | Freedland |
| 4,643,177 A | 2/1987 | Sheppard et al. |
| 4,651,724 A | 3/1987 | Berentey et al. |
| 4,653,487 A | 3/1987 | Maale |
| 4,667,663 A | 5/1987 | Miyata |
| D290,399 S | 6/1987 | Kitchens |
| 4,681,590 A | 7/1987 | Tansey |
| 4,697,585 A | 10/1987 | Williams |
| 4,705,027 A | 11/1987 | Klaue |
| 4,705,032 A | 11/1987 | Keller |
| 4,721,103 A | 1/1988 | Freedland |
| 4,753,657 A | 6/1988 | Lee et al. |
| 4,776,330 A | 10/1988 | Chapman et al. |
| 4,781,181 A | 11/1988 | Tanguy |
| 4,805,595 A | 2/1989 | Kanbara |
| 4,805,607 A | 2/1989 | Engelhardt et al. |
| 4,813,963 A | 3/1989 | Hori et al. |
| 4,817,591 A | 4/1989 | Klaue et al. |
| 4,827,919 A | 5/1989 | Barbarito et al. |
| 4,828,277 A | 5/1989 | De Bastiani et al. |
| 4,854,312 A | 8/1989 | Raftopoulos et al. |
| 4,858,602 A | 8/1989 | Seidel et al. |
| 4,862,883 A | 9/1989 | Freeland |
| 4,871,369 A | 10/1989 | Muller |
| 4,875,475 A | 10/1989 | Comte et al. |
| 4,896,662 A | 1/1990 | Noble |
| 4,921,499 A | 5/1990 | Hoffman et al. |
| 4,927,424 A | 5/1990 | McConnell et al. |
| 4,932,969 A | 6/1990 | Frey et al. |
| 4,943,291 A | 7/1990 | Tanguy |
| 4,946,179 A | 8/1990 | De Bastiani et al. |
| 4,959,066 A | 9/1990 | Dunn et al. |
| 4,969,889 A | 11/1990 | Greig |
| 4,976,258 A | 12/1990 | Richter et al. |
| 4,978,349 A | 12/1990 | Frigg |
| 4,978,358 A | 12/1990 | Bobyn |
| 4,988,349 A | 1/1991 | Pennig |
| 5,002,547 A | 3/1991 | Poggie et al. |
| 5,002,580 A | 3/1991 | Noble et al. |
| 5,006,120 A | 4/1991 | Carter et al. |
| 5,013,314 A | 5/1991 | Firica et al. |
| 5,019,077 A | 5/1991 | De Bastiani et al. |
| 5,026,374 A | 6/1991 | Dezza et al. |
| 5,027,799 A | 7/1991 | Laico et al. |
| 5,030,222 A | 7/1991 | Calandruccio et al. |
| 5,034,012 A | 7/1991 | Frigg |
| 5,034,013 A | 7/1991 | Kyle et al. |
| 5,035,697 A | 7/1991 | Frigg |
| 5,037,423 A | 8/1991 | Kenna |
| 5,041,114 A | 8/1991 | Chapman et al. |
| 5,041,115 A | 8/1991 | Frigg et al. |
| 5,053,035 A | 10/1991 | McLaren |
| 5,057,103 A | 10/1991 | Davis |
| 5,062,854 A | 11/1991 | Noble et al. |
| 5,066,296 A | 11/1991 | Chapman et al. |
| 5,084,050 A | 1/1992 | Draenert |
| 5,092,892 A | 3/1992 | Ashby |
| 5,098,433 A | 3/1992 | Freedland |
| 5,102,413 A | 4/1992 | Poddar |
| 5,108,404 A | 4/1992 | Scholten et al. |
| 5,112,333 A | 5/1992 | Fixel |
| 5,116,335 A | 5/1992 | Hannon et al. |
| 5,116,380 A | 5/1992 | Hewka et al. |
| 5,122,141 A | 6/1992 | Simpson et al. |
| 5,122,146 A | 6/1992 | Chapman et al. |
| 5,124,106 A | 6/1992 | Morr et al. |
| 5,147,408 A | 9/1992 | Noble et al. |
| 5,152,766 A | 10/1992 | Kirkley |
| 5,163,963 A | 11/1992 | Hewka et al. |
| 5,171,324 A | 12/1992 | Campana et al. |
| 5,176,681 A | 1/1993 | Lawes et al. |
| 5,178,621 A | 1/1993 | Cook et al. |
| 5,190,544 A | 3/1993 | Chapman et al. |
| 5,190,546 A | 3/1993 | Jervis |
| 5,192,281 A | 3/1993 | de la Caffiniere |
| 5,197,966 A | 3/1993 | Sommerkamp |
| 5,197,990 A | 3/1993 | Lawes et al. |
| 5,201,735 A | 4/1993 | Chapman et al. |
| 5,201,767 A | 4/1993 | Caldarise et al. |
| 5,263,955 A | 11/1993 | Baumgart et al. |
| 5,268,000 A | 12/1993 | Ottieri et al. |
| 5,281,224 A | 1/1994 | Faccioli et al. |
| 5,292,322 A | 3/1994 | Faccioli et al. |
| 5,295,991 A | 3/1994 | Frigg |
| 5,303,718 A | 4/1994 | Krajicek |
| 5,314,489 A | 5/1994 | Hoffman et al. |
| 5,320,622 A | 6/1994 | Faccioli et al. |
| 5,320,623 A | 6/1994 | Pennig |
| 5,326,376 A | 7/1994 | Warner et al. |
| 5,334,184 A | 8/1994 | Bimman |
| 5,342,360 A | 8/1994 | Faccioli et al. |
| 5,342,362 A | 8/1994 | Kenyon et al. |
| 5,346,496 A | 9/1994 | Pennig |
| 5,350,379 A | 9/1994 | Spievack |
| 5,352,227 A | 10/1994 | O'Hara |
| 5,358,534 A | 10/1994 | Dudasik et al. |
| 5,364,398 A | 11/1994 | Chapman et al. |
| 5,368,594 A | 11/1994 | Martin et al. |
| 5,376,090 A | 12/1994 | Pennig |

| | | |
|---|---|---|
| 5,380,328 A | 1/1995 | Morgan |
| 5,383,932 A | 1/1995 | Wilson et al. |
| 5,387,243 A | 2/1995 | Devanathan |
| 5,397,328 A | 3/1995 | Behrens et al. |
| 5,403,321 A | 4/1995 | DiMarco |
| 5,411,503 A | 5/1995 | Hollstien et al. |
| 5,415,660 A | 5/1995 | Campbell et al. |
| 5,417,695 A | 5/1995 | Axelson, Jr. |
| RE34,985 E | 6/1995 | Pennig |
| 5,433,718 A | 7/1995 | Brinker |
| 5,433,720 A | 7/1995 | Faccioli et al. |
| 5,441,500 A | 8/1995 | Seidel et al. |
| 5,443,477 A | 8/1995 | Marin et al. |
| 5,445,642 A | 8/1995 | McNulty et al. |
| 5,454,813 A | 10/1995 | Lawes |
| 5,454,816 A | 10/1995 | Ashby |
| 5,458,599 A | 10/1995 | Adobbati |
| 5,458,651 A | 10/1995 | Lawes |
| 5,458,653 A | 10/1995 | Davidson |
| 5,472,444 A | 12/1995 | Huebner et al. |
| 5,478,341 A | 12/1995 | Cook et al. |
| 5,480,400 A | 1/1996 | Berger |
| 5,484,438 A | 1/1996 | Pennig |
| 5,484,446 A | 1/1996 | Burke et al. |
| 5,505,734 A | 4/1996 | Caniggia et al. |
| 5,514,137 A | 5/1996 | Coutts |
| 5,516,335 A | 5/1996 | Kummer et al. |
| 5,520,695 A | 5/1996 | Luckman |
| 5,531,748 A | 7/1996 | de la Caffiniere |
| 5,534,004 A | 7/1996 | Santangelo |
| 5,545,162 A | 8/1996 | Huebner |
| 5,549,610 A | 8/1996 | Russell et al. |
| 5,549,706 A | 8/1996 | McCarthy |
| 5,554,192 A | 9/1996 | Crowninshield |
| 5,556,433 A | 9/1996 | Gabriel et al. |
| 5,562,673 A | 10/1996 | Koblish et al. |
| 5,562,674 A | 10/1996 | Stalcup et al. |
| 5,562,675 A | 10/1996 | McNulty et al. |
| 5,571,189 A | 11/1996 | Kuslich |
| 5,571,204 A | 11/1996 | Nies |
| 5,573,536 A | 11/1996 | Grosse et al. |
| 5,578,035 A | 11/1996 | Lin |
| 5,586,985 A | 12/1996 | Putnam et al. |
| 5,591,169 A | 1/1997 | Benoist |
| 5,591,196 A | 1/1997 | Marin et al. |
| 5,593,451 A | 1/1997 | Averill et al. |
| 5,593,452 A | 1/1997 | Higham et al. |
| 5,605,713 A | 2/1997 | Boltong |
| 5,607,431 A | 3/1997 | Dudasik et al. |
| 5,613,970 A | 3/1997 | Houston et al. |
| 5,618,286 A | 4/1997 | Brinker |
| 5,618,300 A | 4/1997 | Marin et al. |
| 5,620,449 A | 4/1997 | Faccioli et al. |
| 5,624,440 A | 4/1997 | Huebner et al. |
| 5,643,258 A | 7/1997 | Robioneck et al. |
| 5,645,545 A | 7/1997 | Bryant |
| 5,645,599 A | 7/1997 | Samani |
| 5,658,283 A | 8/1997 | Huebner |
| 5,658,287 A | 8/1997 | Hofmann et al. |
| 5,658,292 A | 8/1997 | Axelson, Jr. |
| 5,658,293 A | 8/1997 | Vanlaningham |
| 5,658,351 A | 8/1997 | Dudasik et al. |
| 5,662,648 A | 9/1997 | Faccioli et al. |
| 5,662,649 A | 9/1997 | Huebner |
| 5,662,712 A | 9/1997 | Pathak et al. |
| 5,665,090 A | 9/1997 | Rockwood et al. |
| 5,665,091 A | 9/1997 | Noble et al. |
| 5,681,316 A | 10/1997 | DeOrio et al. |
| 5,681,318 A | 10/1997 | Pennig et al. |
| 5,683,389 A | 11/1997 | Orsak |
| 5,683,460 A | 11/1997 | Persoons |
| 5,688,271 A | 11/1997 | Faccioli et al. |
| 5,688,279 A | 11/1997 | McNulty et al. |
| 5,690,634 A | 11/1997 | Muller et al. |
| 5,693,047 A | 12/1997 | Meyers et al. |
| 5,693,048 A | 12/1997 | Stalcup et al. |
| 5,695,729 A | 12/1997 | Chow et al. |
| 5,697,930 A | 12/1997 | Itoman et al. |
| 5,702,215 A | 12/1997 | Li |
| 5,702,481 A | 12/1997 | Lin |
| 5,702,487 A | 12/1997 | Averill et al. |
| 5,707,370 A | 1/1998 | Berki et al. |
| 5,718,704 A | 2/1998 | Medoff |
| 5,728,096 A | 3/1998 | Faccioli et al. |
| 5,741,256 A | 4/1998 | Bresina |
| 5,741,266 A | 4/1998 | Moran et al. |
| 5,749,872 A | 5/1998 | Kyle et al. |
| 5,749,880 A | 5/1998 | Banas et al. |
| 5,759,184 A | 6/1998 | Santangelo |
| 5,766,178 A | 6/1998 | Michielli et al. |
| 5,766,179 A | 6/1998 | Faccioli et al. |
| 5,766,180 A | 6/1998 | Winquist |
| 5,772,662 A | 6/1998 | Chapman et al. |
| 5,776,194 A | 7/1998 | Mikol et al. |
| 5,776,204 A | 7/1998 | Noble et al. |
| 5,779,703 A | 7/1998 | Benoist |
| 5,779,705 A | 7/1998 | Matthews |
| 5,782,921 A | 7/1998 | Colleran et al. |
| 5,785,057 A | 7/1998 | Fischer |
| 5,807,241 A | 9/1998 | Heimberger |
| 5,810,750 A | 9/1998 | Buser |
| 5,810,820 A | 9/1998 | Santori et al. |
| 5,810,830 A | 9/1998 | Noble et al. |
| 5,814,047 A | 9/1998 | Emilio et al. |
| 5,814,681 A | 9/1998 | Hino et al. |
| 5,816,812 A | 10/1998 | Kownacki et al. |
| 5,827,282 A | 10/1998 | Pennig |
| 5,829,081 A | 11/1998 | Pearce |
| 5,836,949 A | 11/1998 | Campbell, Jr. et al. |
| 5,849,004 A | 12/1998 | Bramlet |
| 5,849,014 A | 12/1998 | Mastrorio et al. |
| 5,849,035 A | 12/1998 | Pathak et al. |
| 5,855,581 A | 1/1999 | Koblish et al. |
| 5,863,295 A | 1/1999 | Averill et al. |
| 5,879,352 A | 3/1999 | Filoso et al. |
| 5,881,878 A | 3/1999 | Faccioli et al. |
| 5,882,351 A | 3/1999 | Fox |
| 5,893,850 A | 4/1999 | Cachia |
| 5,895,390 A | 4/1999 | Moran et al. |
| 5,897,560 A | 4/1999 | Johnson |
| 5,902,302 A | 5/1999 | Berki et al. |
| 5,908,422 A | 6/1999 | Bresina |
| 5,908,423 A | 6/1999 | Kashuba et al. |
| 5,912,410 A | 6/1999 | Cordell |
| 5,913,867 A | 6/1999 | Dion |
| 5,919,194 A | 7/1999 | Anderson |
| 5,925,048 A | 7/1999 | Ahmad et al. |
| 5,928,235 A | 7/1999 | Friedl |
| 5,928,240 A | 7/1999 | Johnson |
| 5,928,259 A | 7/1999 | Tovey |
| 5,931,830 A | 8/1999 | Jacobsen et al. |
| 5,931,839 A | 8/1999 | Medoff |
| 5,948,000 A | 9/1999 | Larsen et al. |
| 5,948,001 A | 9/1999 | Larsen |
| 5,951,556 A | 9/1999 | Faccioli et al. |
| 5,951,557 A | 9/1999 | Luter |
| 5,954,722 A | 9/1999 | Bono |
| 5,954,728 A | 9/1999 | Heller et al. |
| 5,964,770 A | 10/1999 | Flomenblit et al. |
| 5,968,047 A | 10/1999 | Reed |
| 5,976,134 A | 11/1999 | Huebner |
| 5,976,147 A | 11/1999 | LaSalle et al. |
| 5,976,188 A | 11/1999 | Dextradeur et al. |
| 5,989,260 A | 11/1999 | Yao |
| 5,989,261 A | 11/1999 | Walker et al. |
| 5,993,459 A | 11/1999 | Larsen et al. |
| 6,004,348 A | 12/1999 | Banas et al. |
| 6,010,505 A | 1/2000 | Asche et al. |
| 6,010,506 A | 1/2000 | Gosney et al. |
| 6,013,081 A | 1/2000 | Burkinshaw et al. |
| 6,015,413 A | 1/2000 | Faccioli et al. |
| 6,017,350 A | 1/2000 | Long |
| 6,019,761 A | 2/2000 | Gustilo |
| 6,019,762 A | 2/2000 | Cole |
| 6,024,745 A | 2/2000 | Faccioli et al. |
| 6,027,506 A | 2/2000 | Faccioli et al. |
| 6,027,534 A | 2/2000 | Wack et al. |
| 6,033,407 A | 3/2000 | Behrens |

| | | | | | | |
|---|---|---|---|---|---|---|
| 6,039,742 A | 3/2000 | Krettek et al. | | 6,491,694 B1 | 12/2002 | Orsak |
| 6,045,556 A | 4/2000 | Cohen | | 6,500,209 B1 | 12/2002 | Kolb |
| 6,053,922 A | 4/2000 | Krause et al. | | 6,508,819 B1 | 1/2003 | Orbay |
| 6,056,756 A | 5/2000 | Eng et al. | | 6,508,820 B2 | 1/2003 | Bales |
| 6,077,264 A | 6/2000 | Chemello | | 6,511,481 B2 | 1/2003 | von Hoffmann et al. |
| 6,080,159 A | 6/2000 | Vichard | | 6,520,994 B2 | 2/2003 | Nogarin |
| 6,093,209 A | 7/2000 | Sanders | | 6,524,313 B1 | 2/2003 | Fassier et al. |
| 6,096,040 A | 8/2000 | Esser | | 6,527,775 B1 | 3/2003 | Warburton |
| 6,102,911 A | 8/2000 | Faccioli et al. | | 6,530,925 B2 | 3/2003 | Boudard et al. |
| 6,106,528 A | 8/2000 | Durham et al. | | 6,533,788 B1 | 3/2003 | Orbay |
| 6,120,504 A | 9/2000 | Brumback et al. | | 6,537,275 B2 | 3/2003 | Venturini et al. |
| 6,120,509 A | 9/2000 | Wheeler | | 6,540,752 B1 | 4/2003 | Hicken et al. |
| 6,126,661 A | 10/2000 | Faccioli et al. | | 6,551,321 B1 | 4/2003 | Burkinshaw et al. |
| 6,126,691 A | 10/2000 | Kasra et al. | | 6,554,833 B2 | 4/2003 | Levy et al. |
| 6,127,597 A | 10/2000 | Beyar et al. | | 6,554,862 B2 | 4/2003 | Hays et al. |
| 6,129,756 A | 10/2000 | Kugler et al. | | 6,558,388 B1 | 5/2003 | Bartsch et al. |
| 6,129,762 A | 10/2000 | Li | | 6,562,042 B2 | 5/2003 | Nelson |
| 6,139,583 A | 10/2000 | Johnson | | 6,565,573 B1 | 5/2003 | Ferrante et al. |
| 6,143,012 A | 11/2000 | Gausepohl | | 6,572,620 B1 | 6/2003 | Schon et al. |
| 6,143,033 A | 11/2000 | Paul et al. | | 6,575,973 B1 | 6/2003 | Shekalim |
| 6,162,223 A | 12/2000 | Orsak et al. | | 6,575,986 B2 | 6/2003 | Overaker |
| 6,162,226 A | 12/2000 | DeCarlo et al. | | 6,575,994 B1 | 6/2003 | Marin et al. |
| 6,168,632 B1 | 1/2001 | Moser et al. | | 6,582,453 B1 | 6/2003 | Tran et al. |
| 6,171,309 B1 | 1/2001 | Huebner | | 6,607,531 B2 | 8/2003 | Frigg |
| 6,176,871 B1 | 1/2001 | Pathak et al. | | 6,613,052 B1 | 9/2003 | Kinnett |
| 6,179,839 B1 | 1/2001 | Weiss et al. | | 6,616,742 B2 | 9/2003 | Lin et al. |
| 6,179,842 B1 | 1/2001 | Spotorno et al. | | 6,620,197 B2 | 9/2003 | Maroney |
| 6,197,029 B1 | 3/2001 | Fujimori et al. | | 6,623,487 B1 | 9/2003 | Goshert |
| 6,197,031 B1 | 3/2001 | Barrette et al. | | 6,629,976 B1 | 10/2003 | Gnos et al. |
| 6,200,321 B1 | 3/2001 | Orbay et al. | | 6,632,224 B2 | 10/2003 | Cachia et al. |
| 6,206,880 B1 | 3/2001 | Karladani | | 6,641,596 B1 | 11/2003 | Lizardi |
| 6,221,036 B1 | 4/2001 | Lucas | | 6,648,889 B2 | 11/2003 | Bramlet et al. |
| 6,221,074 B1 | 4/2001 | Cole et al. | | 6,648,890 B2 | 11/2003 | Culbert et al. |
| 6,224,600 B1 | 5/2001 | Protogirou | | 6,652,529 B2 | 11/2003 | Swanson |
| 6,224,609 B1 | 5/2001 | Ressemann et al. | | 6,652,591 B2 | 11/2003 | Serbousek et al. |
| 6,228,123 B1 | 5/2001 | Dezzani | | 6,656,189 B1 | 12/2003 | Wilson et al. |
| 6,231,576 B1 | 5/2001 | Frigg et al. | | 6,682,568 B2 | 1/2004 | Despres, III et al. |
| 6,235,029 B1 | 5/2001 | Faccioli et al. | | 6,685,679 B2 | 2/2004 | Merdan |
| 6,261,289 B1 | 7/2001 | Levy | | 6,685,706 B2 | 2/2004 | Padget et al. |
| 6,270,499 B1 | 8/2001 | Leu et al. | | 6,688,822 B2 | 2/2004 | Ritter et al. |
| 6,273,876 B1 | 8/2001 | Klima et al. | | 6,695,844 B2 | 2/2004 | Bramlet et al. |
| 6,273,892 B1 | 8/2001 | Orbay et al. | | 6,699,251 B1 | 3/2004 | Venturini |
| 6,280,474 B1 | 8/2001 | Cassidy et al. | | 6,699,253 B2 | 3/2004 | McDowell et al. |
| 6,283,969 B1 | 9/2001 | Grusin et al. | | 6,706,046 B2 | 3/2004 | Orbay et al. |
| 6,287,310 B1 | 9/2001 | Fox | | 6,706,072 B2 | 3/2004 | Dwyer et al. |
| 6,290,725 B1 | 9/2001 | Weiss et al. | | 6,709,436 B1 | 3/2004 | Hover et al. |
| 6,296,603 B1 | 10/2001 | Turnlund et al. | | 6,712,820 B2 | 3/2004 | Orbay |
| 6,296,645 B1 | 10/2001 | Hover et al. | | 6,722,368 B1 | 4/2004 | Shaikh |
| 6,299,642 B1 | 10/2001 | Chan | | 6,723,129 B2 | 4/2004 | Dwyer et al. |
| 6,319,253 B1 | 11/2001 | Ackeret et al. | | 6,730,087 B1 | 5/2004 | Butsch |
| 6,332,886 B1 | 12/2001 | Green et al. | | 6,730,090 B2 | 5/2004 | Orbay et al. |
| 6,336,929 B1 | 1/2002 | Justin | | 6,736,818 B2 | 5/2004 | Perren et al. |
| 6,348,053 B1 | 2/2002 | Cachia | | 6,749,611 B2 | 6/2004 | Venturini et al. |
| 6,355,042 B2 | 3/2002 | Winquist et al. | | 6,755,831 B2 | 6/2004 | Putnam et al. |
| 6,355,069 B1 | 3/2002 | DeCarlo et al. | | 6,755,862 B2 | 6/2004 | Keynan |
| 6,358,250 B1 | 3/2002 | Orbay | | 6,755,866 B2 | 6/2004 | Southworth |
| 6,358,283 B1 | 3/2002 | Hogfors et al. | | 6,767,350 B1 | 7/2004 | Lob |
| 6,364,824 B1 | 4/2002 | Fitzsimmons | | 6,767,351 B2 | 7/2004 | Orbay et al. |
| 6,364,882 B1 | 4/2002 | Orbay | | 6,780,185 B2 | 8/2004 | Frei et al. |
| 6,379,359 B1 | 4/2002 | Dahners | | 6,783,529 B2 | 8/2004 | Hover et al. |
| 6,379,360 B1 | 4/2002 | Ackeret et al. | | 6,783,530 B1 | 8/2004 | Levy |
| 6,395,004 B1 | 5/2002 | Dye et al. | | 6,783,533 B2 | 8/2004 | Green et al. |
| 6,402,753 B1 | 6/2002 | Cole et al. | | 6,786,908 B2 | 9/2004 | Hover et al. |
| 6,406,477 B1 | 6/2002 | Fujiwara | | 6,793,655 B2 | 9/2004 | Orsak |
| 6,416,516 B1 | 7/2002 | Stauch et al. | | 6,793,659 B2 | 9/2004 | Putnam |
| 6,423,096 B1 | 7/2002 | Musset et al. | | 6,808,527 B2 | 10/2004 | Lower et al. |
| 6,425,923 B1 | 7/2002 | Stalcup et al. | | 6,821,299 B2 | 11/2004 | Kirking et al. |
| 6,436,148 B1 | 8/2002 | DeCarlo, Jr. et al. | | 6,827,739 B2 | 12/2004 | Griner et al. |
| 6,440,135 B2 | 8/2002 | Orbay et al. | | 6,827,741 B2 | 12/2004 | Reeder |
| 6,443,954 B1 | 9/2002 | Bramlet et al. | | 6,840,939 B2 | 1/2005 | Venturini et al. |
| 6,443,992 B2 | 9/2002 | Lubinus | | 6,855,146 B2 | 2/2005 | Frigg et al. |
| 6,447,513 B1 | 9/2002 | Griggs | | 6,855,167 B2 | 2/2005 | Shimp et al. |
| 6,447,514 B1 | 9/2002 | Stalcup et al. | | 6,863,692 B2 | 3/2005 | Meulink |
| 6,447,515 B1 | 9/2002 | Meldrum | | 6,866,455 B2 | 3/2005 | Hasler |
| 6,447,518 B1 | 9/2002 | Krause et al. | | 6,866,665 B2 | 3/2005 | Orbay |
| 6,461,358 B1 | 10/2002 | Faccioli | | 6,887,243 B2 | 5/2005 | Culbert |
| 6,461,360 B1 | 10/2002 | Adam | | 6,887,271 B2 | 5/2005 | Justin et al. |
| 6,468,278 B1 | 10/2002 | Muckter | | 6,890,333 B2 | 5/2005 | von Hoffmann et al. |
| 6,488,684 B2 | 12/2002 | Bramlet et al. | | 6,893,444 B2 | 5/2005 | Orbay |

| | | |
|---|---|---|
| 6,908,465 B2 | 6/2005 | von Hoffmann et al. |
| 6,921,397 B2 | 7/2005 | Corcoran et al. |
| 6,926,720 B2 | 8/2005 | Castaneda |
| 6,926,741 B2 | 8/2005 | Kolb |
| 6,929,692 B2 | 8/2005 | Tas |
| 6,942,666 B2 | 9/2005 | Overaker et al. |
| 6,942,668 B2 | 9/2005 | Padget et al. |
| 6,949,100 B1 | 9/2005 | Venturini |
| 6,949,124 B2 | 9/2005 | Serbousek et al. |
| 6,951,561 B2 | 10/2005 | Warren et al. |
| 6,974,482 B2 | 12/2005 | Zhu |
| 6,986,771 B2 | 1/2006 | Paul et al. |
| 7,001,388 B2 | 2/2006 | Orbay et al. |
| D518,174 S | 3/2006 | Venturini et al. |
| 7,008,425 B2 | 3/2006 | Phillips |
| 7,008,428 B2 | 3/2006 | Cachia et al. |
| 7,008,451 B2 | 3/2006 | Justin et al. |
| 7,011,664 B2 | 3/2006 | Haney et al. |
| 7,012,106 B2 | 3/2006 | Yuan et al. |
| 7,029,476 B2 | 4/2006 | Hansson |
| 7,029,478 B2 | 4/2006 | Hollstien et al. |
| 7,033,363 B2 | 4/2006 | Powell |
| 7,033,365 B2 | 4/2006 | Powell et al. |
| 7,041,104 B1 | 5/2006 | Cole et al. |
| 7,044,978 B2 | 5/2006 | Howie et al. |
| 7,052,498 B2 | 5/2006 | Levy et al. |
| 7,056,322 B2 | 6/2006 | Davison et al. |
| 7,060,075 B2 | 6/2006 | Govari et al. |
| 7,070,601 B2 | 7/2006 | Culbert et al. |
| 7,070,616 B2 | 7/2006 | Majercak et al. |
| 7,074,224 B2 | 7/2006 | Daniels et al. |
| 7,083,624 B2 | 8/2006 | Irving |
| 7,090,676 B2 | 8/2006 | Huebner et al. |
| 7,097,648 B1 | 8/2006 | Globerman et al. |
| 7,097,664 B2 | 8/2006 | Despres, III et al. |
| RE39,301 E | 9/2006 | Bertin |
| 7,101,376 B2 | 9/2006 | Semet |
| 7,118,574 B2 | 10/2006 | Patel et al. |
| 7,122,056 B2 | 10/2006 | Dwyer et al. |
| 7,137,987 B2 | 11/2006 | Patterson et al. |
| 7,141,052 B2 | 11/2006 | Manderson |
| 7,141,067 B2 | 11/2006 | Jones et al. |
| 7,144,399 B2 | 12/2006 | Hayes et al. |
| 7,147,639 B2 | 12/2006 | Berki et al. |
| 7,147,640 B2 | 12/2006 | Huebner et al. |
| 7,153,309 B2 | 12/2006 | Huebner et al. |
| 7,156,852 B2 | 1/2007 | Dye et al. |
| 7,160,302 B2 | 1/2007 | Warburton |
| 7,160,333 B2 | 1/2007 | Plouhar et al. |
| 7,163,563 B2 | 1/2007 | Schwartz et al. |
| 7,175,625 B2 | 2/2007 | Culbert |
| 7,175,631 B2 | 2/2007 | Wilson et al. |
| 7,179,260 B2 | 2/2007 | Gerlach et al. |
| 7,188,687 B2 | 3/2007 | Rudd et al. |
| 7,189,237 B2 | 3/2007 | Huebner |
| 7,632,277 B2 | 12/2009 | Woll et al. |
| 7,846,162 B2 | 12/2010 | Nelson et al. |
| 7,909,825 B2 * | 3/2011 | Saravia et al. ............... 606/66 |
| 7,914,533 B2 | 3/2011 | Nelson et al. |
| 7,942,875 B2 | 5/2011 | Nelson et al. |
| 2001/0034526 A1 | 10/2001 | Kuslich et al. |
| 2002/0161369 A1 | 10/2002 | Bramlet et al. |
| 2002/0188297 A1 | 12/2002 | Dakin et al. |
| 2003/0040752 A1 | 2/2003 | Kitchens |
| 2003/0045919 A1 | 3/2003 | Swoyer et al. |
| 2003/0236529 A1 | 12/2003 | Shluzas et al. |
| 2004/0133204 A1 | 7/2004 | Davies |
| 2004/0213825 A1 | 10/2004 | Levy |
| 2004/0214311 A1 | 10/2004 | Levy |
| 2004/0230193 A1 | 11/2004 | Cheung et al. |
| 2005/0015154 A1 | 1/2005 | Lindsey et al. |
| 2005/0027294 A1 | 2/2005 | Woll et al. |
| 2005/0027301 A1 | 2/2005 | Stihl |
| 2005/0047892 A1 | 3/2005 | Bremner |
| 2005/0080425 A1 | 4/2005 | Bhatnagar et al. |
| 2005/0159749 A1 | 7/2005 | Levy et al. |
| 2005/0165395 A1 | 7/2005 | Orbay et al. |
| 2005/0177158 A1 | 8/2005 | Doubler et al. |
| 2005/0216007 A1 | 9/2005 | Woll et al. |
| 2005/0228391 A1 | 10/2005 | Levy et al. |
| 2005/0261781 A1 | 11/2005 | Sennett et al. |
| 2005/0267481 A1 | 12/2005 | Carl et al. |
| 2006/0015101 A1 | 1/2006 | Warburton et al. |
| 2006/0015123 A1 | 1/2006 | Fencl et al. |
| 2006/0036248 A1 | 2/2006 | Ferrante |
| 2006/0064094 A1 | 3/2006 | Levy et al. |
| 2006/0084998 A1 | 4/2006 | Levy et al. |
| 2006/0200143 A1 | 9/2006 | Warburton |
| 2006/0200144 A1 | 9/2006 | Warburton |
| 2006/0229617 A1 | 10/2006 | Meller et al. |
| 2006/0247638 A1 | 11/2006 | Trieu et al. |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2007/0142916 A1 | 6/2007 | Olson et al. |
| 2007/0233105 A1 | 10/2007 | Nelson et al. |
| 2008/0132896 A1 | 6/2008 | Bowen et al. |
| 2008/0140078 A1 | 6/2008 | Nelson et al. |
| 2008/0149115 A1 | 6/2008 | Hauck et al. |
| 2008/0161805 A1 | 7/2008 | Saravia et al. |
| 2008/0221620 A1 | 9/2008 | Krause |
| 2008/0255560 A1 | 10/2008 | Myers et al. |
| 2008/0262495 A1 | 10/2008 | Doubler et al. |
| 2008/0287951 A1 * | 11/2008 | Stoneburner et al. ........... 606/63 |
| 2009/0018542 A1 | 1/2009 | Saravia et al. |
| 2009/0228007 A1 | 9/2009 | Justin et al. |
| 2009/0228008 A1 | 9/2009 | Justin et al. |
| 2010/0023010 A1 | 1/2010 | Nelson et al. |
| 2011/0087227 A1 | 4/2011 | Mazur et al. |
| 2011/0144645 A1 | 6/2011 | Saravia et al. |
| 2011/0282346 A1 | 11/2011 | Pham et al. |

FOREIGN PATENT DOCUMENTS

| | | |
|---|---|---|
| EP | 1582163 A1 | 11/2003 |
| EP | 1815813 A2 | 8/2007 |
| WO | WO 97/18769 A1 | 5/1997 |
| WO | WO 98/27876 A1 | 7/1998 |
| WO | WO 98/56301 A1 | 12/1998 |
| WO | WO 99/20195 A1 | 4/1999 |
| WO | WO 00/28906 A1 | 5/2000 |
| WO | WO 01/28443 A1 | 4/2001 |
| WO | WO 02/00270 A1 | 1/2002 |
| WO | WO 02/00275 A1 | 1/2002 |
| WO | WO 02/02158 A1 | 1/2002 |
| WO | WO 2005/112804 A1 | 12/2005 |
| WO | WO 2006/053210 A1 | 5/2006 |
| WO | WO 2006/124764 A1 | 11/2006 |

OTHER PUBLICATIONS

The Titanium Flexible Humeral Nail System (Quick reference for surgical technique), Synthes, 1999.

The Titanium Flexible Humeral Nail System (Technique Guide), Synthes, 1999.

Nelson et al.; U.S. Appl. No. 12/482,395 entitled "Fracture fixation device, tools and methods," filed Jun. 10, 2009.

Nelson et al.; U.S. Appl. No. 12/482,406 entitled "Fracture fixation device, tools and methods," filed Jun. 10, 2009.

US 6,030,385, 02/2000, Faccioli et al. (withdrawn)

* cited by examiner

ND METHODS", filed Jul. 11, 2007.

FRACTURE FIXATION DEVICE, TOOLS AND METHODS

CROSS-REFERENCE TO RELATED APPLICATIONS

This application is a Continuation-in-Part of U.S. application Ser. No. 11/383,269, titled "MINIMALLY INVASIVE ACTUABLE BONE FIXATION DEVICES", filed May 15, 2006 now U.S. Pat. No. 7,846,162 which claims priority to U.S. Provisional Application No. 60/682,652, titled "METHOD AND SYSTEM FOR PROVIDING REINFORCEMENT OF BONES", filed May 18, 2005. This application is also a Continuation-in-part of U.S. application Ser. No. 11/383,800 filed May 17, 2006 now abandoned, titled "DEPLOYABLE INTRAMEDULLARY STENT SYSTEM FOR REINFORCEMENT OF BONE" which claims priority to U.S. Provisional Application No. 60/682,652, titled "METHOD AND SYSTEM FOR PROVIDING REINFORCEMENT OF BONES", filed May 18, 2005. This application is also a Continuation-in-Part of U.S. application Ser. No. 11/944,366, titled "FRACTURE FIXATION DEVICE, TOOLS AND METHODS", filed Nov. 21, 2007 now U.S. Pat. No. 7,909,825 which claims priority to U.S. provisional applications: No. 60/867,011, titled "BONE REPAIR IMPLANT WITH CENTRAL RATCHETING GUIDEWIRE", filed Nov. 22, 2006; No. 60/866,976, titled "SURGICAL TOOLS FOR USE IN DEPLOYING BONE REPAIR DEVICES," filed Nov. 22, 2006; and No. 60/949,071, titled "FRACTURE FIXATION DEVICE, TOOLS AND METHODS", filed Jul. 11, 2007.

This application claims priority of U.S. Provisional Application No. 61/060,440, titled "FRACTURE FIXATION DEVICE, TOOLS AND METHODS" filed Jun. 10, 2008; U.S. Provisional Application No. 61/060,445, titled "FRACTURE FIXATION DEVICE, TOOLS AND METHODS" filed Jun. 10, 2008; U.S. Provisional Application No. 61/060,450, titled "FRACTURE FIXATION DEVICE, TOOLS AND METHODS" filed Jun. 10, 2008; U.S. Provisional Application No. 61/100,635, titled "FRACTURE FIXATION DEVICE, TOOLS AND METHODS" filed Sep. 26, 2008; U.S. Provisional Application No. 61/100,652, titled "FRACTURE FIXATION DEVICE, TOOLS AND METHODS" filed Sep. 26, 2008; U.S. Provisional Application No. 61/122,563, titled "BONE FIXATION DEVICE, TOOLS AND METHODS" filed Dec. 15, 2008; U.S. Provisional Application No. 61/138,920, titled "BONE FIXATION DEVICE, TOOLS AND METHODS" filed Dec. 18, 2008; and U.S. Provisional Application No. 61/117,901, titled "BONE FRACTURE FIXATION SCREWS, SYSTEMS AND METHODS OF USE" filed Nov. 25, 2008.

INCORPORATION BY REFERENCE

All publications and patent applications mentioned in this specification are herein incorporated by reference to the same extent as if each individual publication or patent application was specifically and individually indicated to be incorporated by reference

BACKGROUND OF THE INVENTION

The present invention relates to devices, tools and methods for providing reinforcement of bones. More specifically, the present invention relates to devices, tools and methods for providing reconstruction and reinforcement of bones, including diseased, osteoporotic and fractured bones. The number and diversity of sport and work related fractures are being driven by several sociological factors. The diversity of high energy sports has increased and the participation in these sports has followed the general trend of affluence and the resultant amount of time for leisure. High energy sports include skiing, motorcycle riding, snow mobile riding, snowboarding, mountain biking, road biking, kayaking, and all terrain vehicle (ATV) riding. As the general affluence of the economically developed countries has increased the number and age of people participating in these activities has increased. Lastly, the acceptance and ubiquitous application of passive restraint systems, airbags, in automobiles has created greater numbers of non-life threatening fractures. In the past, a person that might expire from a serious automobile accident now survives with multiple traumas and resultant fractures.

Bone fractures are a common medical condition both in the young and old segments of the population. However, with an increasingly aging population, osteoporosis has become more of a significant medical concern in part due to the risk of osteoporotic fractures. Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass, leading to fractures in more than 300,000 people over the age of 65. In 1997 the estimated cost for osteoporosis related fractures was $13 billion. That figure increased to $17 billion in 2002 and is projected to increase to $210-240 billion by 2040. Currently it is expected that one in two women, and one in four men, over the age of 50 will suffer an osteoporosis-related fracture. Osteoporosis is the most important underlying cause of fracture in the elderly. Also, sports and work-related accidents account for a significant number of bone fractures seen in emergency rooms among all age groups.

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (IM) rod or nail is used to align and stabilize the fracture. In that instance, a metal rod is placed inside a canal of a bone and fixed in place, typically at both ends. See, for example, Fixion™ IM(Nail), www.disc-o-tech.com. Placement of conventional IM rods are typically a "line of sight" and require access collinear with the center line of the IM canal. Invariably, this line of sight access violates, disrupts, and causes damage to important soft tissue structures such as ligaments, tendons, cartilage, facia, and epidermis This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, and or when the nail is not removed, a long term implant of the IM nail. The outer diameter of the IM nail must be selected for the minimum inside diameter of the space. Therefore, portions of the IM nail may not be in contact with the canal. Further, micromotion between the bone and the IM nail may cause pain or necrosis of the bone. In still other cases, infection can occur.

The IM nail may be removed after the fracture has healed. This requires a subsequent surgery with all of the complications and risks of a later intrusive procedure. In general, rigid IM rods or nails are difficult to insert, can damage the bone and require additional incisions for cross-screws to attach the rods or nails to the bone.

Some IM nails are inflatable. See, for example, Meta-Fix IM Nailing System, www.disc-o-tech.com. Such IM nails require inflating the rod with very high pressures, endangering the surrounding bone. Inflatable nails have many of the same drawbacks as the rigid IM nails described above, while improving the ease of insertion, eliminating cross-screw incisions and minimizing trauma.

External fixation is another technique employed to repair fractures. In this approach, a rod may traverse the fracture site outside of the epidermis. The rod is attached to the bone with trans-dermal screws. If external fixation is used, the patient will have multiple incisions, screws, and trans-dermal infection paths. Furthermore, the external fixation is cosmetically intrusive, bulky, and prone to painful inadvertent manipulation by environmental conditions such as, for example, bumping into objects and laying on the device.

Other concepts relating to bone repair are disclosed in, for example, U.S. Pat. No. U.S. Pat. No. 5,108,404 to Scholten for Surgical Protocol for Fixation of Bone Using Inflatable Device; U.S. Pat. No. 4,453,539 to Raftopoulos et al. for Expandable Intramedullary Nail for the Fixation of Bone Fractures; U.S. Pat. No. 4,854,312 to Raftopolous for Expanding Nail; U.S. Pat. No. 4,932,969 to Frey et al. for Joint Endoprosthesis; U.S. Pat. No. 5,571,189 to Kuslich for Expandable Fabric Implant for Stabilizing the Spinal Motion Segment; U.S. Pat. No. 4,522,200 to Stednitz for Adjustable Rod; U.S. Pat. No. 4,204,531 to Aginsky for Nail with Expanding Mechanism; U.S. Pat. No. 5,480,400 to Berger for Method and Device for Internal Fixation of Bone Fractures; U.S. Pat. No. 5,102,413 to Poddar for Inflatable Bone Fixation Device; U.S. Pat. No. 5,303,718 to Krajicek for Method and Device for the Osteosynthesis of Bones; U.S. Pat. No. 6,358,283 to Hogfors et al. for Implantable Device for Lengthening and Correcting Malpositions of Skeletal Bones; U.S. Pat. No. 6,127,597 to Beyar et al. for Systems for Percutaneous Bone and Spinal Stabilization, Fixation and Repair; U.S. Pat. No. 6,527,775 to Warburton for Interlocking Fixation Device for the Distal Radius; U.S. Patent Publication US2006/0084998 A1 to Levy et al. for Expandable Orthopedic Device; and PCT Publication WO 2005/112804 A1 to Myers Surgical Solutions, LLC et. al. for Fracture Fixation and Site Stabilization System. Other fracture fixation devices, and tools for deploying fracture fixation devices, have been described in: U.S. Patent Appl. Publ. No. 2006/0254950; U.S. Ser. No. 60/867,011 (filed Nov. 22, 2006); U.S. Ser. No. 60/866,976 (filed Nov. 22, 2006); and U.S. Ser. No. 60/866,920 (filed Nov. 22, 2006).

In view of the foregoing, it would be desirable to have a device, system and method for providing effective and minimally invasive bone reinforcement and fracture fixation to treat fractured or diseased bones.

SUMMARY OF THE INVENTION

Aspects of the invention relate to embodiments of a bone fixation device and to methods for using such a device for repairing a bone fracture. The bone fixation device may include an elongate body with a longitudinal axis, having a flexible state and a rigid state. The device further may include a plurality of grippers disposed at longitudinally-spaced locations along the elongated body, a rigid hub connected to the elongated body, and an actuator that is operably-connected to the grippers to deploy the grippers from a first shape to an expanded second shape. The elongate body and the rigid hub may or may not be collinear or parallel.

In one embodiment, a bone fixation device is provided with an elongate body having a longitudinal axis and having a first state in which at least a portion of the body is flexible and a second state in which the body is generally rigid, an actuatable bone engaging mechanism disposed on the elongate body, and an actuator operably connected to the bone engaging mechanism to actuate the bone engaging mechanism from a disengaged configuration to an engaged configuration.

Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone.

Another such method of repairing a fracture of a clavicle, the clavicle having a lateral segment adjacent to the acromion of a scapula and a medial segment adjacent to the manubrium of a sternum comprises creating an intramedullary channel, such that the channel traverses the fracture of the clavicle and comprises at least one segment that substantially follows a curved anatomical contour of the clavicle; and inserting a bone fixation device into the intramedullary channel and across the fracture of the clavicle, such that at least a portion of an elongate body of the fixation device in a flexible state is placed within the curved segment of the channel.

According to aspects of the present disclosure, similar methods involve repairing a fracture of a metatarsal, metacarpal, sternum, tibia, rib, midshaft radius, ulna, olecranon (elbow), huberus, or distal fibula. Each of these bones have a distal and proximal segment, farthest and closest to the heart, respectively, and on opposite ends of a fracture. The method comprises creating an intramedullary channel, such that the channel traverses the fracture of the bone and comprises at least one segment that substantially follows a curved anatomical contour of the bone; and inserting a bone fixation device into the intramedullary channel and across the fracture of the bone, such that at least a portion of an elongate body of the fixation device in a flexible state is placed within the curved segment of the channel.

One embodiment of the present invention provides a low weight to volume mechanical support for fixation, reinforcement and reconstruction of bone or other regions of the musculo-skeletal system in both humans and animals. The method of delivery of the device is another aspect of the invention. The method of delivery of the device in accordance with the various embodiments of the invention reduces the trauma created during surgery, decreasing the risks associated with infection and thereby decreasing the recuperation time of the patient. The framework may in one embodiment include an expandable and contractible structure to permit re-placement and removal of the reinforcement structure or framework.

In accordance with the various embodiments of the present invention, the mechanical supporting framework or device may be made from a variety of materials such as metal, composite, plastic or amorphous materials, which include, but are not limited to, steel, stainless steel, cobalt chromium plated steel, titanium, nickel titanium alloy (nitinol), super-elastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In still another embodiment of the invention, a method of repairing a bone fracture is disclosed that comprises: accessing a fracture along a length of a bone through a bony protuberance at an access point at an end of a bone; advancing a bone fixation device into a space through the access point at the end of the bone; bending a portion of the bone fixation device along its length to traverse the fracture; and locking the bone fixation device into place within the space of the bone. The method can also include the step of advancing an obturator through the bony protuberance and across the fracture prior to advancing the bone fixation device into the space. In yet another embodiment of the method, the step of anchoring the bone fixation device within the space can be included.

An aspect of the invention discloses a removable bone fixation device that uses a single port of insertion and has a single-end of remote actuation wherein a bone fixation device stabilizes bone after it has traversed the fracture. The bone fixation device is adapted to provide a single end in one area or location where the device initiates interaction with bone. The device can be deployed such that the device interacts with bone. Single portal insertion and single-end remote actuation enables the surgeon to insert and deploy the device, deactivate and remove the device, reduce bone fractures, displace or compress the bone, and lock the device in place. In addition, the single-end actuation enables the device to grip bone, compresses the rigidizable flexible body, permits axial, torsional and angular adjustments to its position during surgery, and releases the device from the bone during its removal procedure. A removable extractor can be provided in some embodiments of the device to enable the device to be placed and extracted by deployment and remote actuation from a single end. The device of the invention can be adapted and configured to provide at least one rigidizable flexible body or sleeve. Further the body can be configured to be flexible in all angles and directions. The flexibility provided is in selective planes and angles in the Cartesian, polar, or cylindrical coordinate systems. Further, in some embodiments, the body is configured to have a remote actuation at a single end. Additionally, the body can be configured to have apertures, windings, etc. The device may be configured to function with non-flexible bodies for use in bones that have a substantially straight segment or curved segments with a constant radius of curvature. Another aspect of the invention includes a bone fixation device in that has mechanical geometry that interacts with bone by a change in the size of at least one dimension of a Cartesian, polar, or spherical coordinate system. Further, in some embodiments, bioabsorbable materials can be used in conjunction with the devices, for example by providing specific subcomponents of the device configured from bioabsorbable materials. A sleeve can be provided in some embodiments where the sleeve is removable, has deployment, remote actuation, and a single end. Where a sleeve is employed, the sleeve can be adapted to provide a deployable interdigitation process or to provide an aperture along its length through which the deployable interdigitation process is adapted to engage bone. In some embodiments, the deployable interdigitation process is further adapted to engage bone when actuated by the sleeve. In some embodiments, the bone fixation device further comprises a cantilever adapted to retain the deployable bone fixation device within the space. The sleeve can further be adapted to be expanded and collapsed within the space by a user. One end of the device can be configured to provide a blunt obturator surface adapted to advance into the bone. A guiding tip may also be provided that facilitates guiding the device through the bone. The device may be hollow and accept a guide wire. The guiding tip may facilitate placement of the device thereby providing a means to remove bone in its path (a helical end, a cutting end, or ablative end). The guiding tip may allow capture, interaction, or insertion into or around a tube on its internal or external surface. Further, the deployable bone fixation device can be adapted to receive external stimulation to provide therapy to the bone. The device can further be adapted to provide an integral stimulator which provides therapy to the bone. In still other embodiments, the device can be adapted to receive deliver therapeutic stimulation to the bone.

The devices disclosed herein may be employed in various regions of the body, including: spinal, cranial, thoracic, lower extremities and upper extremities. Additionally, the devices are suitable for a variety of breaks including, epiphyseal, metaphyseal, diaphyseal cortical bone, cancellous bone, and soft tissue such as ligament attachment and cartilage attachment.

The fracture fixation devices of various embodiments of the invention are adapted to be inserted through an opening of a fractured bone, such as the radius (e.g., through a bony protuberance on a distal or proximal end or through the midshaft) into a intramedullary canal of the bone. The device can be inserted in one embodiment in a line of sight manner collinear or nearly collinear, or parallel to the central axis of the intramedullary canal. In another embodiment, the device can be inserted at an angle, radius, or tangency to the axis of the intramedullary canal. In another embodiment, the device can be inserted in a manner irrespective of the central axis of the intramedullary canal. In some embodiments, the fixation device has two main components, one configured component for being disposed on the side of the fracture closest to the opening and one component configured for being disposed on the other side of the fracture from the opening so that the fixation device traverses the fracture.

The device components cooperate to align, fix and/or reduce the fracture so as to promote healing. The device may be removed from the bone after insertion (e.g., after the fracture has healed or for other reasons), or it may be left in the bone for an extended period of time or permanently.

In some embodiments, the fracture fixation device has one or more actuatable bone engaging mechanisms such as anchors or grippers on its proximal and/or distal ends. These bone engaging mechanisms may be used to hold the fixation device to the bone while the bone heals. In another embodiment, the fracture fixation device has a plurality of actuatable bone engaging mechanisms such as grippers or anchors along its length. In another embodiment, the fracture fixation device has grippers or anchoring devices that interdigitate into the bone at an angle greater than zero degrees and less than 180 degrees to secure the bone segments of the fracture. In another embodiment the fracture fixation device has grippers or anchoring features that when activated from a state that facilitates insertion to a state that captures, aligns, and fixes the fracture, deploy in a geometry so that the resultant fixed bone is analogous or nearly identical, or identical to the geometry of the bone prior to the fracture, anatomical configuration. In one embodiment of the device, the flexible body allows insertion through tortuous paths within bone or created within bone. Upon activation from the state of insertion to the state of fixation, this device deforms so as to grip the bone upon multiple surfaces of the now collapsed, rigid, flexible body. In this collapsed state the device may be deform in such a way to re-achieve anatomical alignment of the bone. The device as described above can be fabricated so that it can have any cross sectional shape. Examples of cross sectional shapes include round, oval, square, rectangular, n-sided, where n is an integer from 1 to infinity, star shaped, spoke shaped.

In some embodiments, to aid in insertion into the intramedullary canal, at least one component of the fracture fixation device has a substantially flexible state and a substantially rigid state. Once in place, deployment of the device also causes the components to change from the flexible state to a rigid state to aid in proper fixation of the fracture. At least one of the components may be substantially rigid or semi-flexible. At least one component may provide a bone screw attachment site for the fixation device.

In some embodiments, to aid in insertion of the device into the intramedullary canal, the main component of the fracture fixation device has a substantially flexible state. Thereby, the device, prior to activation, may not have a rigid section. Once in place, deployment of the device also causes the components to change from the flexible state to a rigid state to aid in proper fixation of the fracture. At least one of the components may be semi-flexible. Placement of the device may be aided by a detachable rigid member such as a guide or outrigger. Placement of the device may be aided by removable rigid member such as a tube or guide wire. At least one component may provide a bone screw attachment site for the fixation device. At least one of the components of the device may allow a screw or compressive member to be attached along its axis to provide linear compression of one side of the fractured bone towards the other (e.g. compression of the distal segment towards the proximal segment or visa versa). At least one of the components of the device may accept a screw at an acute angle, and angle less than 30 degrees from the axis of the device that would allow compression of one side of the fractured bone towards the other. At least one of the components of the device may accept an alternately removable eyelet to accommodate a compressive device so as to compress one side of the fractured bone towards the other side.

Embodiments of the invention also provide deployment tools with a tool guide for precise alignment of one or more bone screws with the fracture fixation device. These embodiments also provide bone screw orientation flexibility so that the clinician can select an orientation for the bone screw(s) that will engage the fixation device as well as any desired bone fragments or other bone or tissue locations.

These and other features and advantages of the present invention will be understood upon consideration of the following detailed description of the invention and the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

By way of background and to provide context for the invention, it may be useful to understand that bone is often described as a specialized connective tissue that serves three major functions anatomically. First, bone provides a mechanical function by providing structure and muscular attachment for movement. Second, bone provides a metabolic function by providing a reserve for calcium and phosphate. Finally, bone provides a protective function by enclosing bone marrow and vital organs. Bones can be categorized as long bones (e.g. radius, femur, tibia and humerus) and flat bones (e.g. skull, scapula and mandible). Each bone type has a different embryological template. Further each bone type contains cortical and trabecular bone in varying proportions. The devices of this invention can be adapted for use in any of the bones of the body as will be appreciated by those skilled in the art.

Cortical bone (compact) forms the shaft, or diaphysis, of long bones and the outer shell of flat bones. The cortical bone provides the main mechanical and protective function. The trabecular bone (cancellous) is found at the end of the long bones, or the epiphysis, and inside the cortex of flat bones. The trabecular bone consists of a network of interconnecting trabecular plates and rods and is the major site of bone remodeling and resorption for mineral homeostasis. During development, the zone of growth between the epiphysis and diaphysis is the metaphysis. Finally, woven bone, which lacks the organized structure of cortical or cancellous bone, is the first bone laid down during fracture repair. Once a bone is fractured, the bone segments are positioned in proximity to each other in a manner that enables woven bone to be laid down on the surface of the fracture. This description of anatomy and physiology is provided in order to facilitate an understanding of the invention. Persons of skill in the art will also appreciate that the scope and nature of the invention is not limited by the anatomy discussion provided. Further, it will be appreciated there can be variations in anatomical characteristics of an individual patient, as a result of a variety of factors, which are not described herein. Further, it will be appreciated there can be variations in anatomical characteristics between bones which are not described herein.

While the inventive devices, tools and methods described herein may be adapted for use with many regions of the musculo-skeletal system in both humans and animals, they are particularly well suited for addressing fractures in the human clavicle, also known as the collar bone. Clavicle fractures involve approximately 5% of all fractures seen in hospital emergency admissions. The clavicle is most commonly fractured between the proximal ⅔ and distal ⅓ of its length. Fractures often occur when a patient falls onto an outstretched upper extremity, falls onto a shoulder, or receives direct clavicular trauma.

Figure 1:
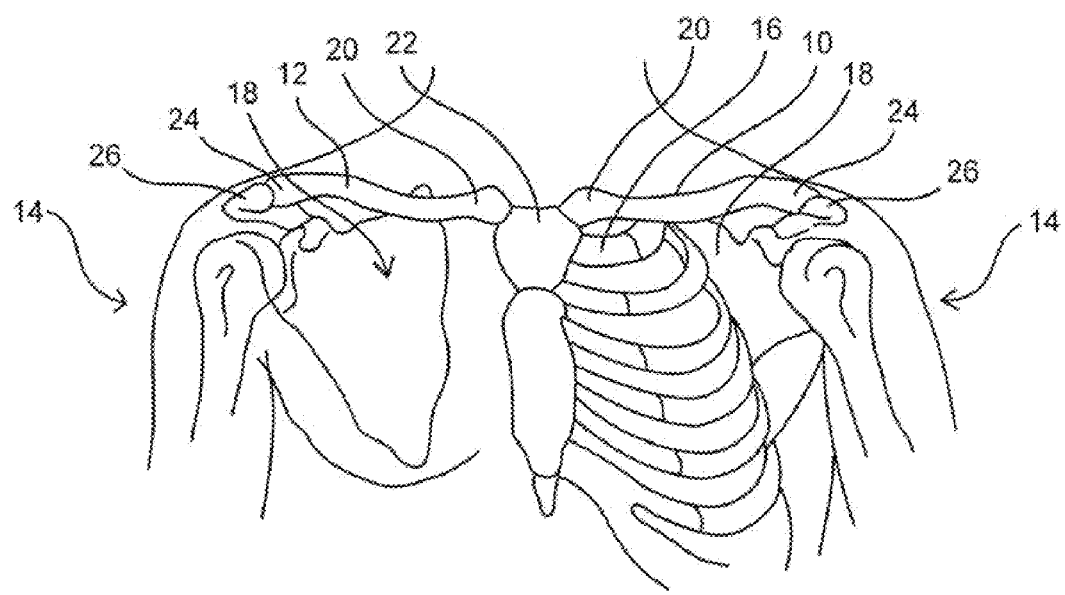
FIG. 1 depicts the skeletal system of the pectoral girdles.

FIG. 1 shows the location of the left clavicle 10 and right clavicle 12 in the human anatomy. The clavicle is classified as a membranous bone that makes up part of the pectoral girdles 14. The clavicle receives its name from the Latin claviculam, meaning "little key", because the bone rotates along its axis like a key when the shoulder is abducted. This movement is palpable with the opposite hand. The clavicle is a doubly curved short bone that connects the arm (upper limb) to the body (trunk), located directly above the first rib 16. It acts as a shunt to keep the scapula 18 in position so the arm can hang freely. At its medial end 20, the clavicle 10, 12 articulates with the manubrium of the sternum 22 (breast-bone) at the sternoclavicular joint. At its lateral end 24, the clavicle 10, 12 articulates with the acromion 26 of the scapula (shoulder blade) at the acromioclavicular joint. As mentioned, the clavicle is a double curved bone, comprising a lateral segment having a lateral curve and a medial segment having a medical curve. It has been found by Jonas Andermahr et al. in "*Anatomy of the clavicle and the Intramedullary Nailing of Midclavicular Fractures*" (*Clinical Anatomy* 20 (2007): 48-56), that the medial curve radius is about 7.1±1.3 cm overall (N=196) with women (N=106) having a slightly smaller curvature of 7.0±1.2 cm and men (N=90) having a slightly larger curvature of 7.3±1.3 cm. The lateral curve radius is about 3.9±1.4 cm overall (N=196) with women (N=106) having a slightly larger curvature of 4.2±1.6 cm and men (N=90) having a slightly smaller curvature of 3.6±1.1 cm.

Figure 2:
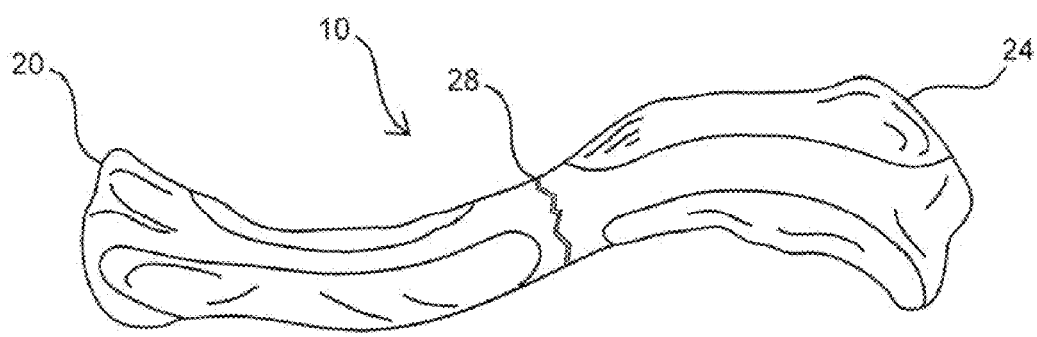
FIG. 2 show the superior surface of a left clavicle.

FIG. 2 is an enlarged view of the superior surface of the left clavicle 10. As can be seen, the clavicle 10 has a rounded medial end (sternal extremity) 20 and a flattened lateral end (acromial extremity) 24. From the roughly pyramidal sternal end 20, clavicle 10 curves laterally and posteriorly for roughly half its length. It then forms a smooth posterior curve to articulate with a process of the scapula (acromion), as described above. The flat, acromial end 24 of the clavicle 10 is broader than the sternal end 20. The acromial end 24 has a rough inferior surface that bears prominent lines and tubercles. These surface features are attachment sites for muscles and ligaments of the shoulder. The clavicle is made up of spongy (cancellous) bone with a shell of compact bone. It is a dermal bone derived from elements originally attached to the skull. An exemplary mid-shaft fracture site 28 is depicted in FIG. 2.

Figure 3:
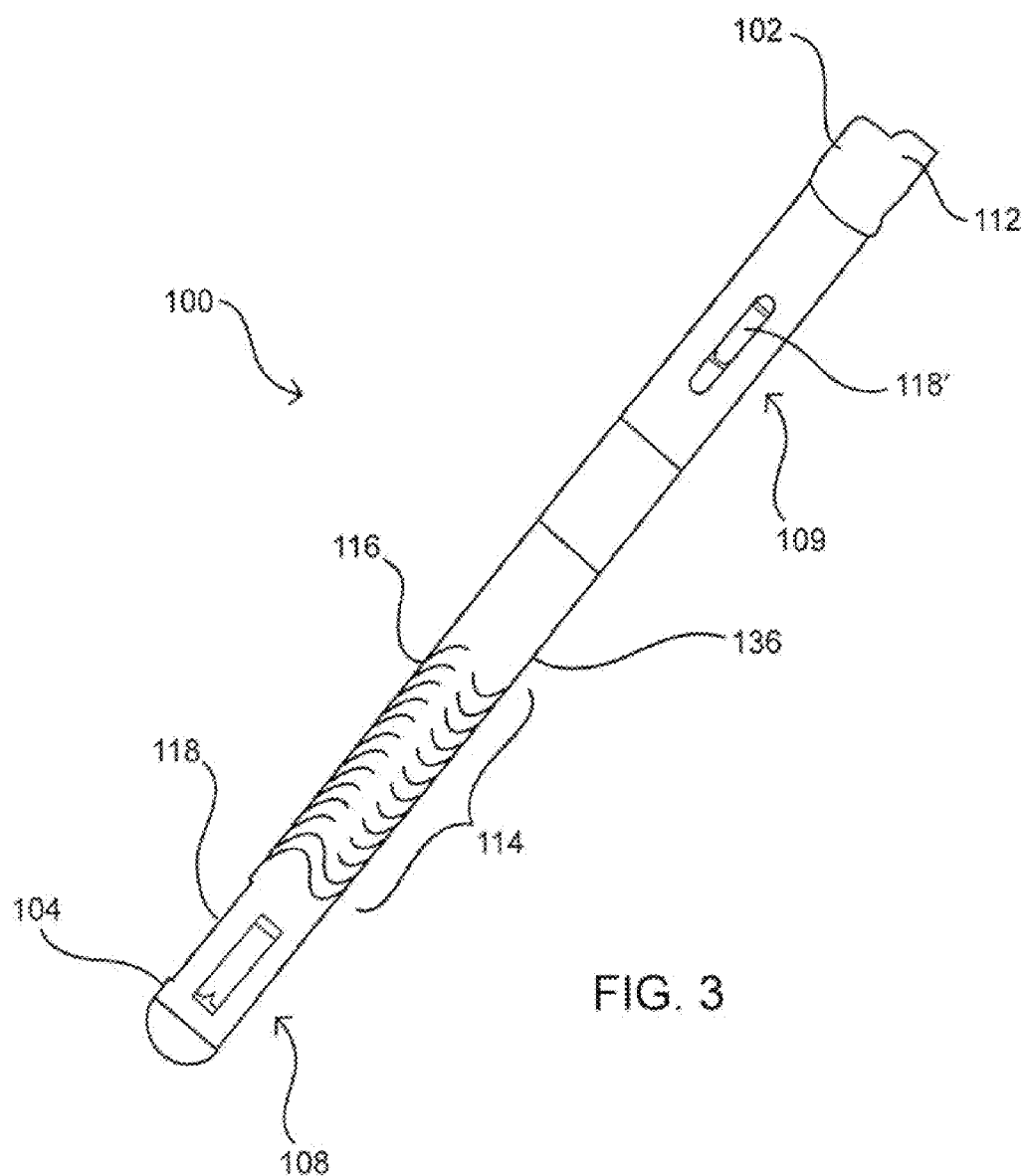
FIG. 3 is a side view of an embodiment of a bone repair device constructed according to aspects of the invention.
Figure 4:
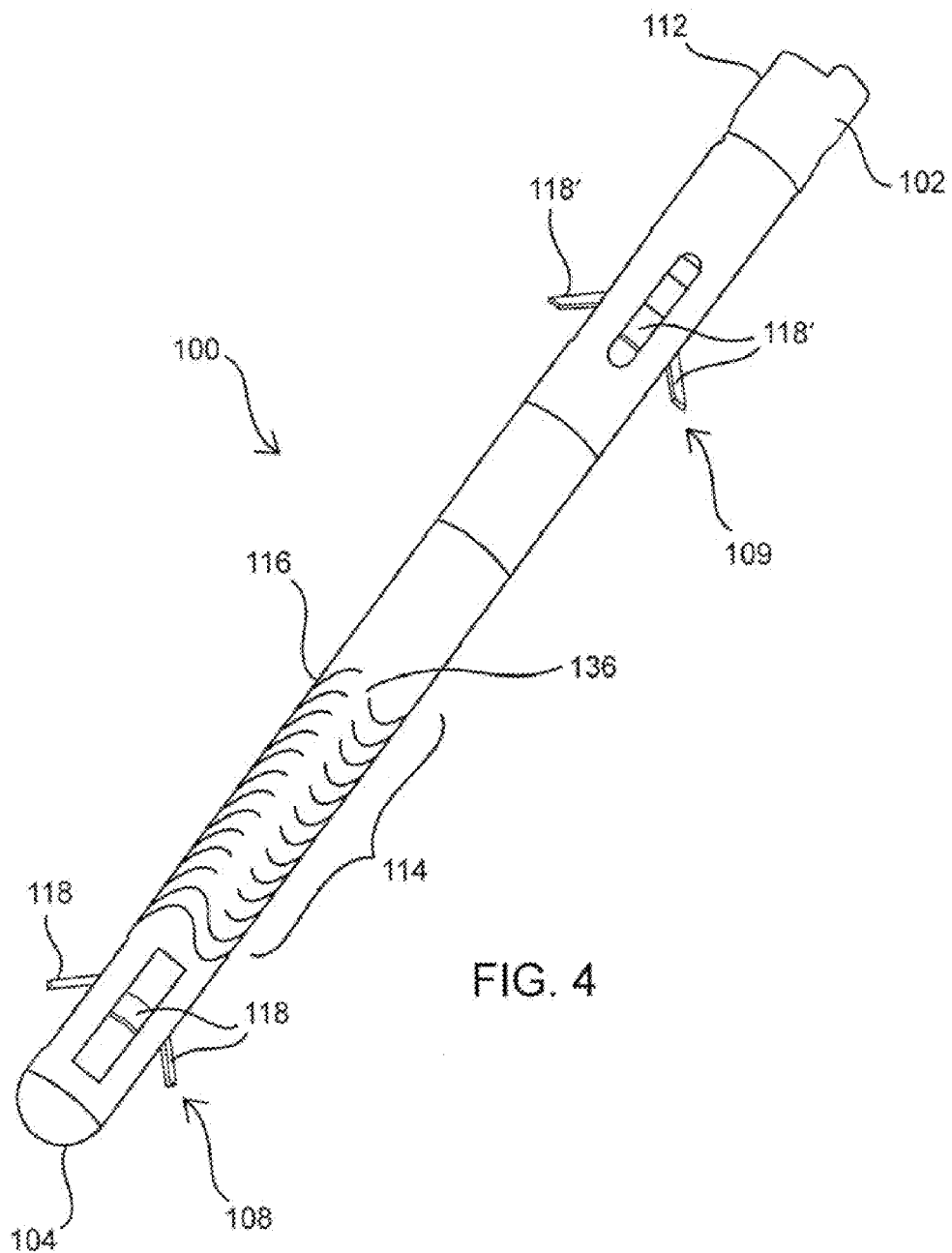
FIG. 4 shows the device of FIG. 3 in a deployed state.

FIGS. 3 and 4 show an exemplary embodiment of a fracture fixation device according to aspects of the invention. As will be later described, device 100 may be implanted in a longitudinal intramedullary cavity of clavicle 10 shown in FIG. 2, or other bones, to approximate and/or secure fracture 28. FIG. 3 shows device 100 in a retracted state for insertion into or removal from a bone, while FIG. 4 shows the device in an expanded state as when it is anchored within a bone.

Bone repair device 100 has a proximal end 102 (nearest the surgeon) and a distal end 104 (further from surgeon) and positioned within the bone space of a patient according to the invention. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference. As described in most instances herein, the device will be implanted into a bone, such as a clavicle, such that the proximal end will be implanted in the lateral segment of the clavicle bone, and the distal end will be implanted in the medial segment of the clavicle bone.

When implanted within a patient, the device can be held in place with suitable fasteners such as wire, screws, nails, bolts, nuts and/or washers. The device 100 may be used for fixation of fractures of the proximal or distal end of long bones such as intracapsular, intertrochanteric, intercervical, supracondular, or condular fractures of the femur; for fusion of a joint; or for surgical procedures that involve cutting a bone. The devices 100 may be implanted or attached through the skin so that a pulling force (traction may be applied to the skeletal system).

Figure 15:
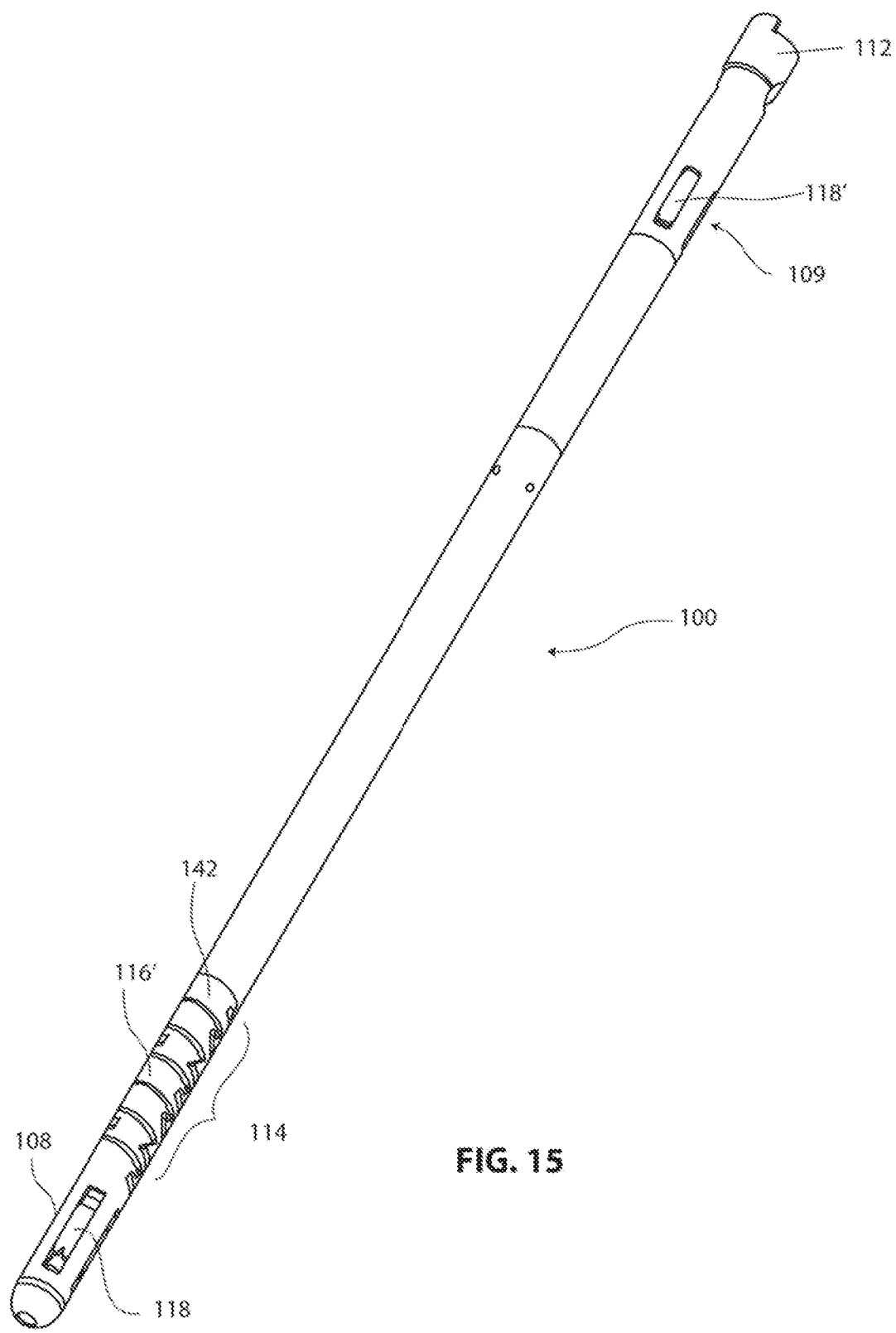
FIG. 15 is a perspective view of an alternative embodiment.

In the embodiment shown in FIGS. 3, 4, and 15, the design of the repair device 100 depicted is adapted to provide two bone engaging mechanisms or grippers 108, 109, each adapted to engage target bone of a patient from the inside of the bone. As configured for this anatomical application, the device is designed to facilitate bone healing when placed in the intramedullary space within a post fractured bone. This device 100 has a gripper 108 positioned distally, and another gripper 109 positioned proximally. Both grippers are deployed radially outward against the wall of the intramedullary cavity. On entry into the cavity, grippers 108, 109 are flat and retracted as shown in FIG. 3. Upon deployment, grippers 108, 109 pivot radially outward, as shown in FIG. 4, and grip the diaphyseal bone in this embodiment from the inside of the bone. One or more screws 110, shown in FIG. 11, placed through apertures through the hub 112 lock the device 100 to the metaphyseal bone. Hence, the proximal end and or metaphysis and the distal end and or diaphysis are joined. The union between the proximal and distal ends may be achieved by the grippers 108 and 109 alone or in concert with screws 110 placed through hub 112. Hub 112 may be either at the distal or proximal end of the bone, in this case clavicle. A hub 112 may be at both ends of the device, there by allowing screws to be placed in the distal and proximal ends. A flexible-to-rigid body portion 114 may also be provided, and in this embodiment is positioned between grippers 108 and 109.

The flexible-to-rigid body portion may be placed proximal or distal to both grippers, 108 and 109. It may be provided with cut 116 that is specific for the purpose and location of the device, as will be described in more detail below.

Figure 5:
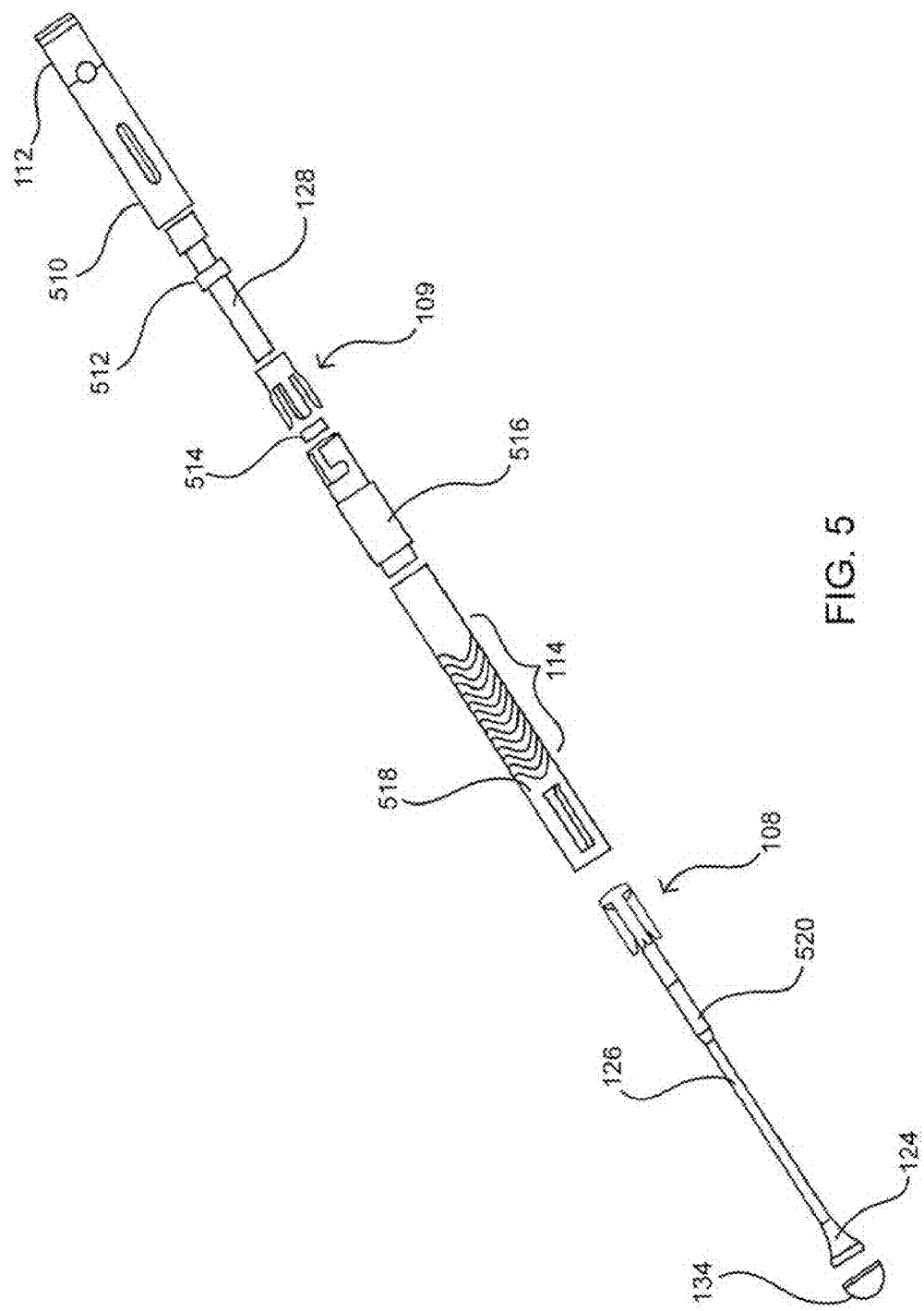
FIG. 5 is an exploded view showing the components of the device shown in FIG. 3.

FIG. 5 shows an exploded view of device 100. In this embodiment, device 100 (starting at the proximal end and moving towards the distal end) is formed from a proximal body member 510, drive member 128, keeper ring 512, proximal gripper 109, bushing 514, coupling member 516, distal body member 518, distal gripper 108, actuator 126, and tip cover 134. During assembly of device 100, proximal gripper 109 is rotatably received over the reduced diameter portion of drive member 128 until it abuts against the larger diameter proximal portion of drive member 128. Keeper ring 512 is then slid over the reduced diameter portion of drive member 128 to the position shown and is welded, pinned, press fit, swaged, adhered and/or otherwise secured in place such that it allows gripper 128 to rotate with respect to drive member 128 but not move axially relative to it. Bushing 514 is similarly slid over the reduced diameter portion of drive member 128 and secured in a position more distal than keeper ring 512. This drive member/gripper assembly is then placed within the axial bore of proximal body member 516.

Each end of coupling member 516 has a stepped portion of smaller outer diameter than the middle of coupling member 516. During assembly, the longer, proximal end of coupling member 516 is received within the distal end of proximal body member 510 (after the drive member/gripper assembly is inserted, as described above). The shorter, distal end of coupling member 516 is received within the proximal end of distal body member 518. The proximal and distal body members 510,518 are secured to coupling member 516, such as by welding or other suitable means. When assembled, proximal body member 510, coupling member 516, and distal body member 518 form a smooth tube having a generally constant outer diameter, as shown in FIG. 3.

Distal gripper 108 is configured to fit within the distal end of distal body member 518. The proximal end of actuator 126 may be passed through the center of distal gripper 108, distal body member 518, and coupling member 516 until it reaches drive member 128, which is rotatably housed within proximal body member 510. The distal end of drive member 128 includes an internally threaded bore for receiving the externally threaded proximal end of actuator 126. As drive member 128 is rotated with respect to actuator 126, actuator 126 moves proximally and/or drive member 128 moves distally. Mating features of actuator 126 and coupling member 516, as will be later described, allow actuator 126 to move axially but prevent it from rotating.

Figure 17:
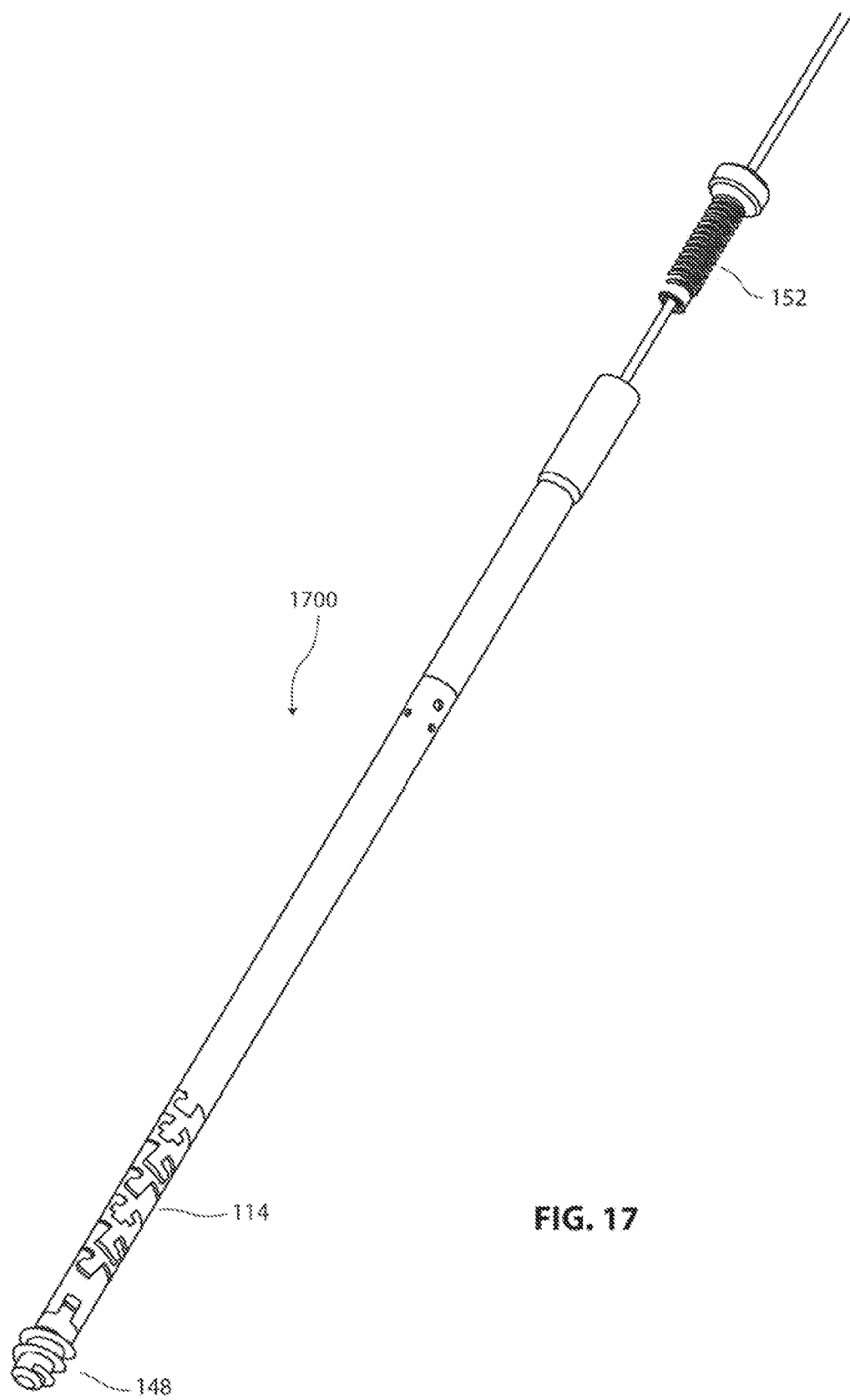
FIGS. 17 and 18 are a perspective view and a cross-section view, respectively, of an alternative embodiment.
Figure 19:
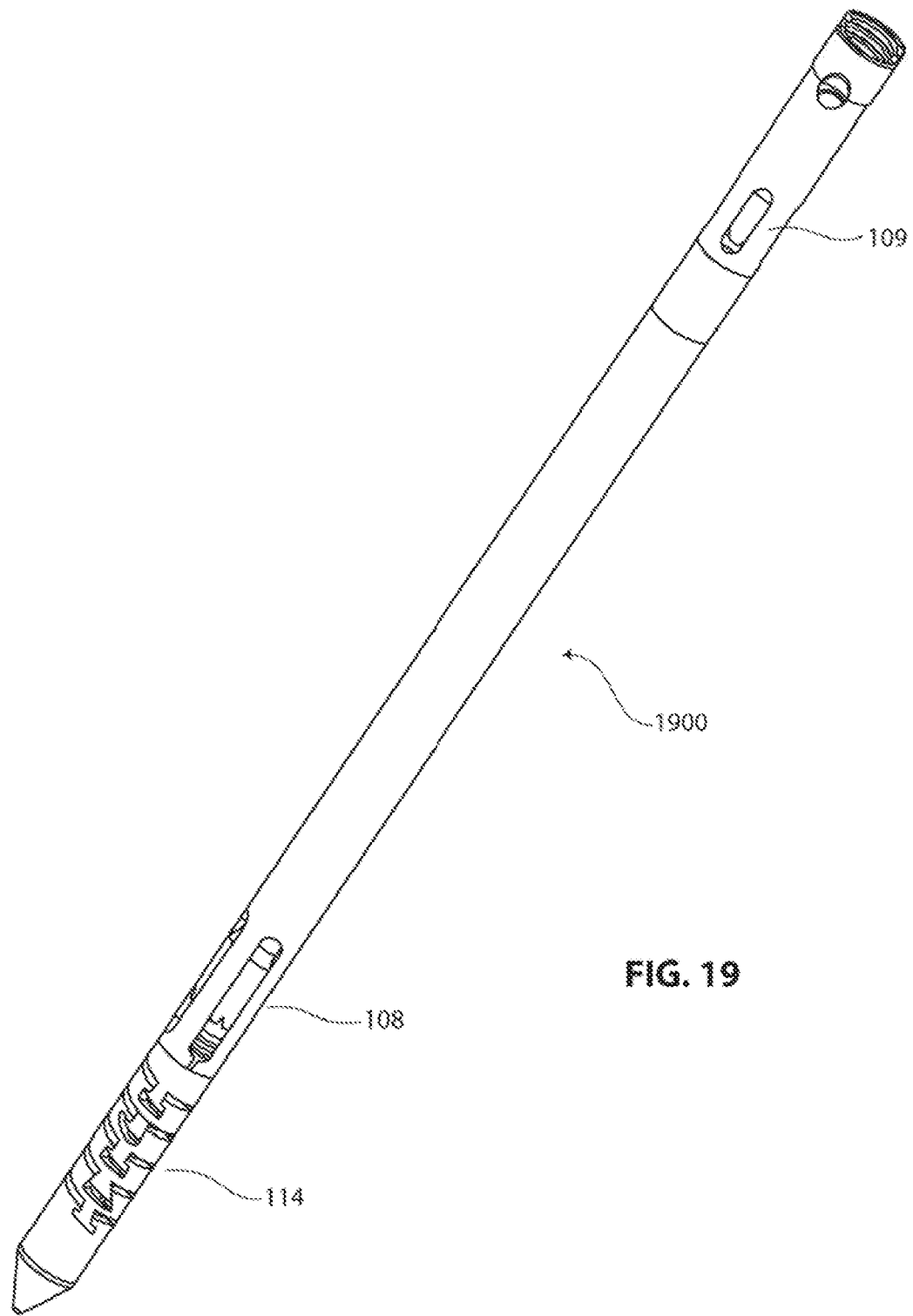
FIGS. 19 and 20 are a side view and a cross-section view, respectively, of an alternative embodiment.

The assembly of device 100 may be completed by attaching hemispherical tip cover 134 to the distal end of distal body member 518, such as by welding or other suitable process. Tip cover 134 may be configured to act as a blunt obturator. This arrangement facilitates penetration of bone by device 100 while keeping the tip of device 100 from digging into bone during an insertion procedure. Alternatively, as shown in FIG. 17, the tip may include a screw or threaded tip or, as shown in FIG. 19, the tip may have a conical shape. The tip may have various geometrical configurations that adapt to enabling tools such as guide wires and guide tubes. The tip may be actively coupled to an electrical or mechanical source that removes or ablates bone to facilitate insertion. Variations or alternatives to the exemplary assembly procedure described above will be apparent to those skilled in the art.

Figure 6A:
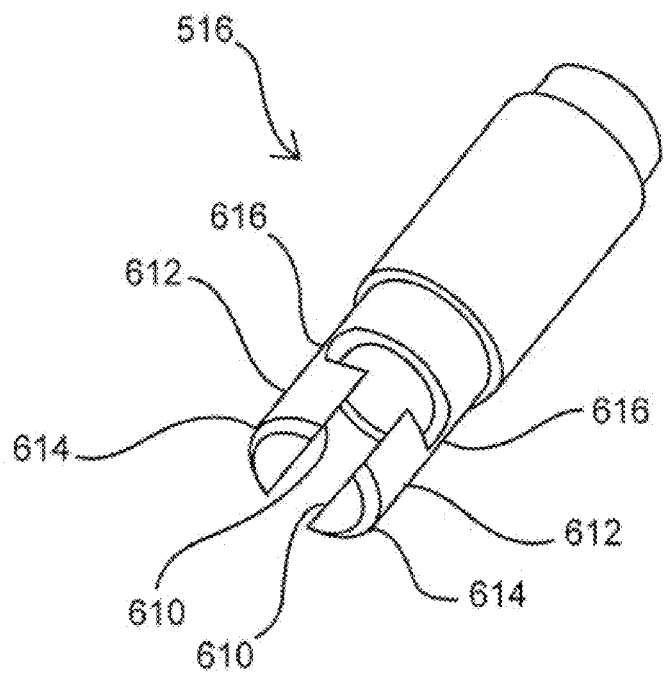
FIGS. 6A and 6B are perspective views showing a coupling member.
Figure 6B:
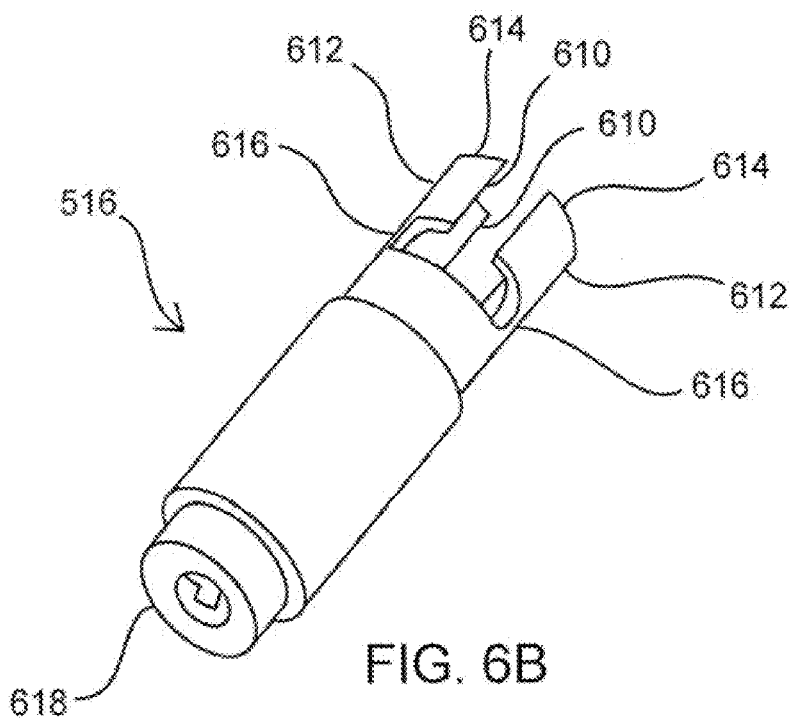

FIGS. 6A and 6B show detailed features of coupling member 516. T-shaped slots 610, 610 are formed on opposite sides of the proximal end of coupling member 516. This leaves two T-shaped appendages 612, 612 which extend in a proximal direction from coupling member 516 when it is assembled in device 100. The outer edges of each T-shaped appendage 612 include a ramped surface 614, 614, the purpose of which will be later described. The inner end of each T-shaped appendage 612 is connected to the main body of coupling member 516 by a necked down portion 616, 616. The necked down portions 616, 616 are configured and arranged to bend, allowing T-shaped appendages 612, 612 to pivot axially inward, as will be later described.

The distal end of coupling member 516 is provided with an oblong axial slot 618. The parallel sides of slot 618 mate with the flattened portion 520 of actuator 126 (shown in FIG. 5) to allow actuator 126 to move axially but prevent it from rotating.

Figure 7A:
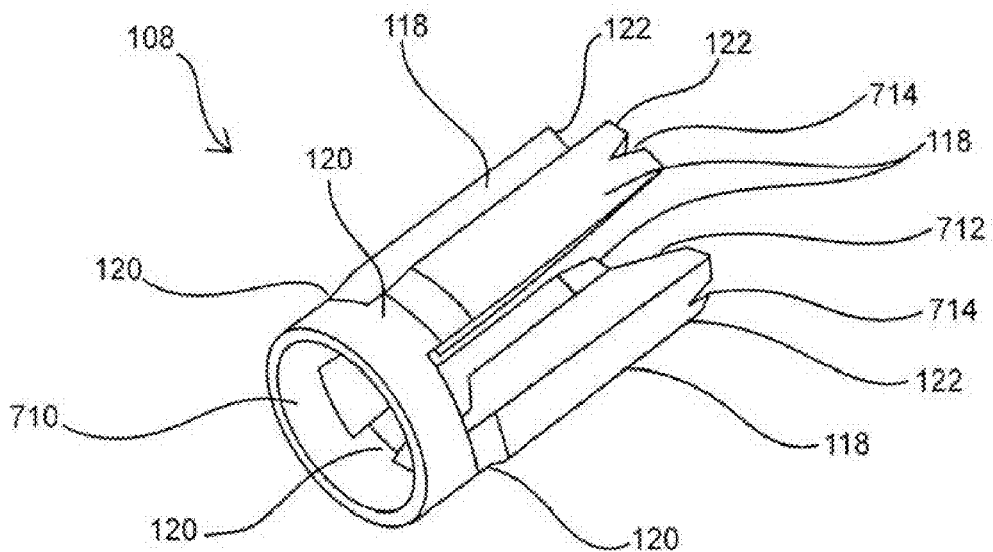
FIGS. 7A and 7B are perspective views showing a distal gripper.
Figure 7B:
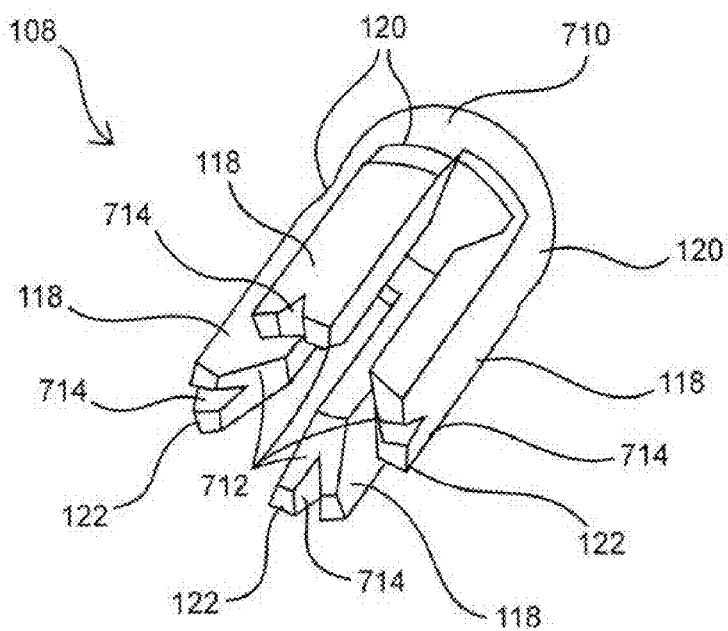

FIGS. 7A and 7B show detailed features of distal gripper 108. Gripper 108 includes two pairs of opposing bendable members 118. Each bendable member 118 has a thinned portion 120 that connects it to a common collar 710. Thinned portions 120 permit bending as the opposite distal ends 122 of members 118 are urged radially outward, such that members 118 may pivot about thinned portions 120. When radially extended, distal ends 122 of bendable members 118 contact the inside of the bone to anchor the distal portion of device 100 to the bone, as will be later described. As shown, each distal end 122 includes a ramped surface 712 to assist in radial deployment, and a notch 714 to assist in engaging the inner surface of the bone. In other embodiments, the notch 714 may be replaced with a point, radii, or rectangular geometry. In some embodiments ramped surface 712 is omitted. In other embodiments, it has an angle selected between 0 and 90 degrees. In other embodiments, this surface may have multiple angles between 0 and 90 degree, thereby faceting. This faceting may allow the expansion to be staged by tactile feedback. In still other embodiments, the ramped surface is curved and has a radius of between 0 and 1.0 inches. In other embodiments, there may be multiple radii. The ramped surface may be located on other surfaces of bendable member 118. Gripper 108 may have 1, 2, 3, 4, 5, 6, or some number of bendable members 118 that can be accommodated by the geometry of the device. In some embodiments, gripper 108 may be made of a nickel-titanium alloy.

Figure 8A:
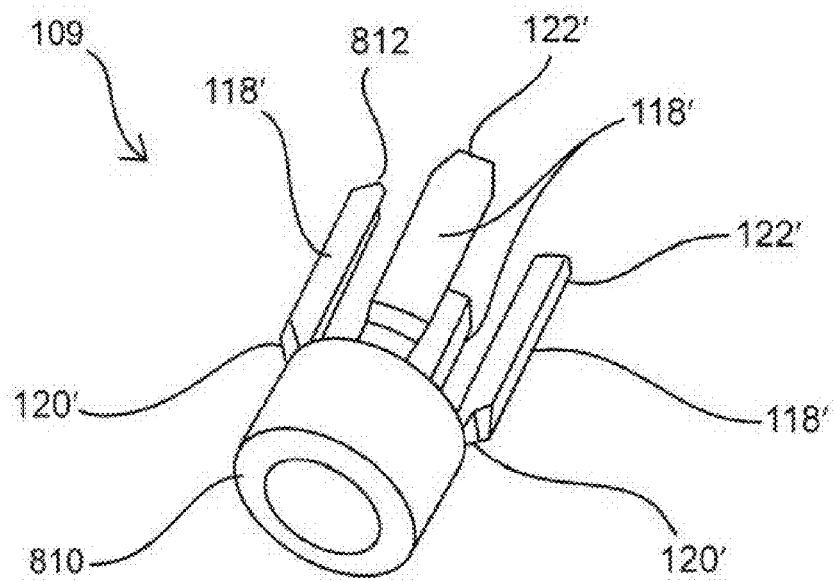
FIGS. 8A and 8B are perspective views showing a proximal gripper.
Figure 8B:
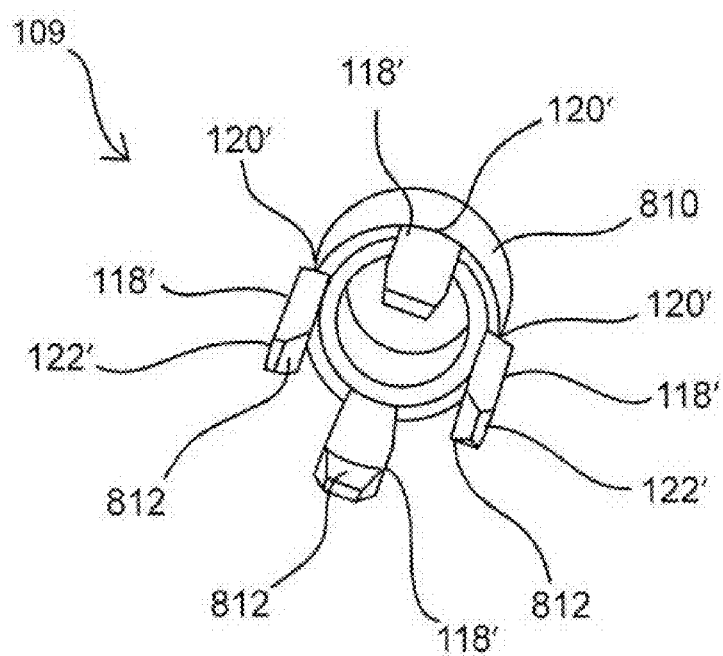

FIGS. 8A and 8B show detailed features of proximal gripper 109. Proximal gripper 109 has a construction and operation similar to those of distal gripper 108. Gripper 109 includes two pairs of opposing bendable members 118'. Each bendable member 118' has a thinned portion 120' that connects it to a common collar 810. Thinned portions 120' permit bending as the opposite distal ends 122' of members 118' are urged radially outward, such that members 118' may pivot about thinned portions 120'. When radially extended, distal ends 122' of bendable members 118' contact the inside of the bone to anchor the distal portion of device 100 to the bone, as will be later described. As shown, each distal end 122' includes a ramped surface 812 to assist in radial deployment. In some embodiments ramped surface 812 is omitted. In other embodiments, it has an angle selected between 0 and 90 degrees. In still other embodiments, the ramped surface is curved and has a radius of between 0 and 1.0 inches. The ramped surface may be located on other surfaces of bendable member 118'. In some embodiments, gripper 109 may be made of a nickel-titanium alloy. In some embodiments, one or more grippers may each comprise 1, 2, 3, 4, 5, 6 or more bendable members similar to members 118 or 118' shown. In some embodiments, gripper 109 may be made of a nickel-titanium alloy.

Figure 9:
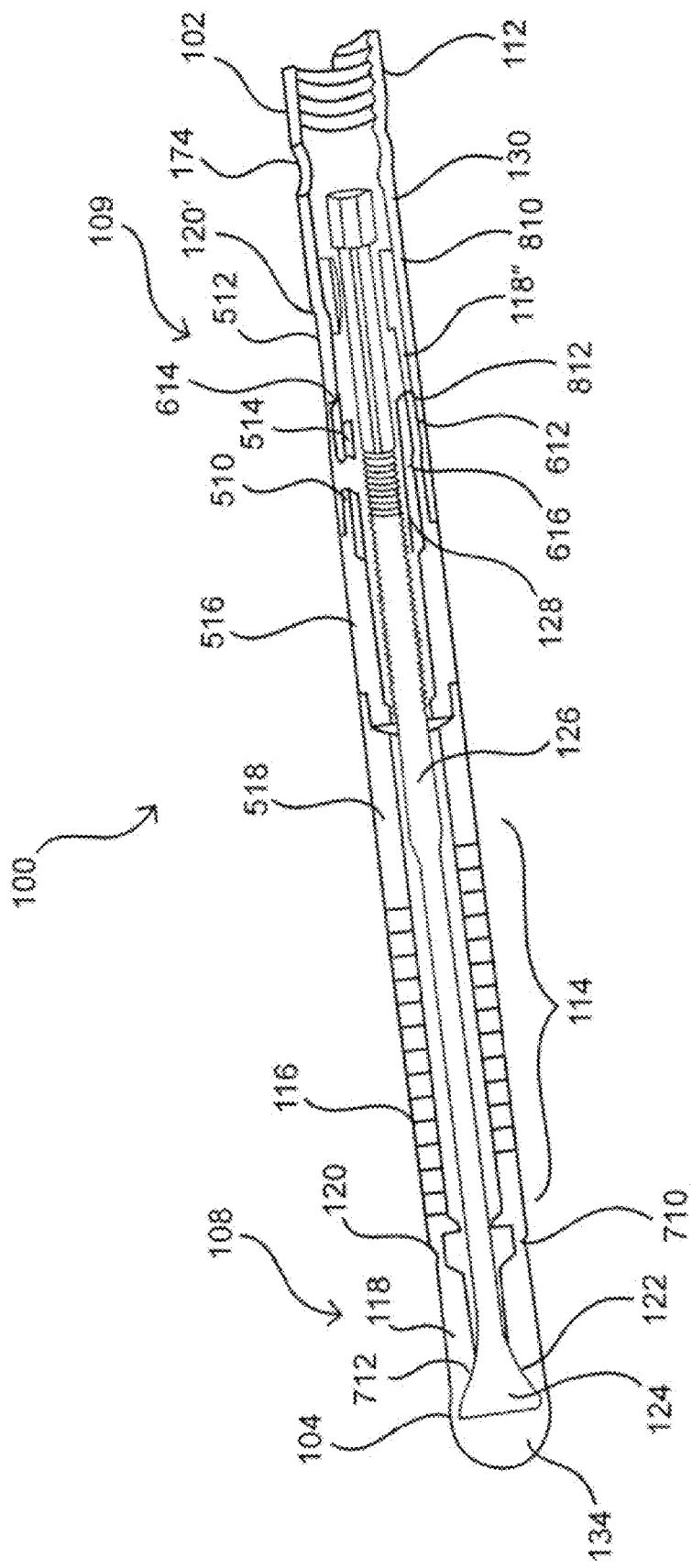
FIG. 9 is a cross-section view of the device of FIG. 3 in a retracted state.
Figure 10:
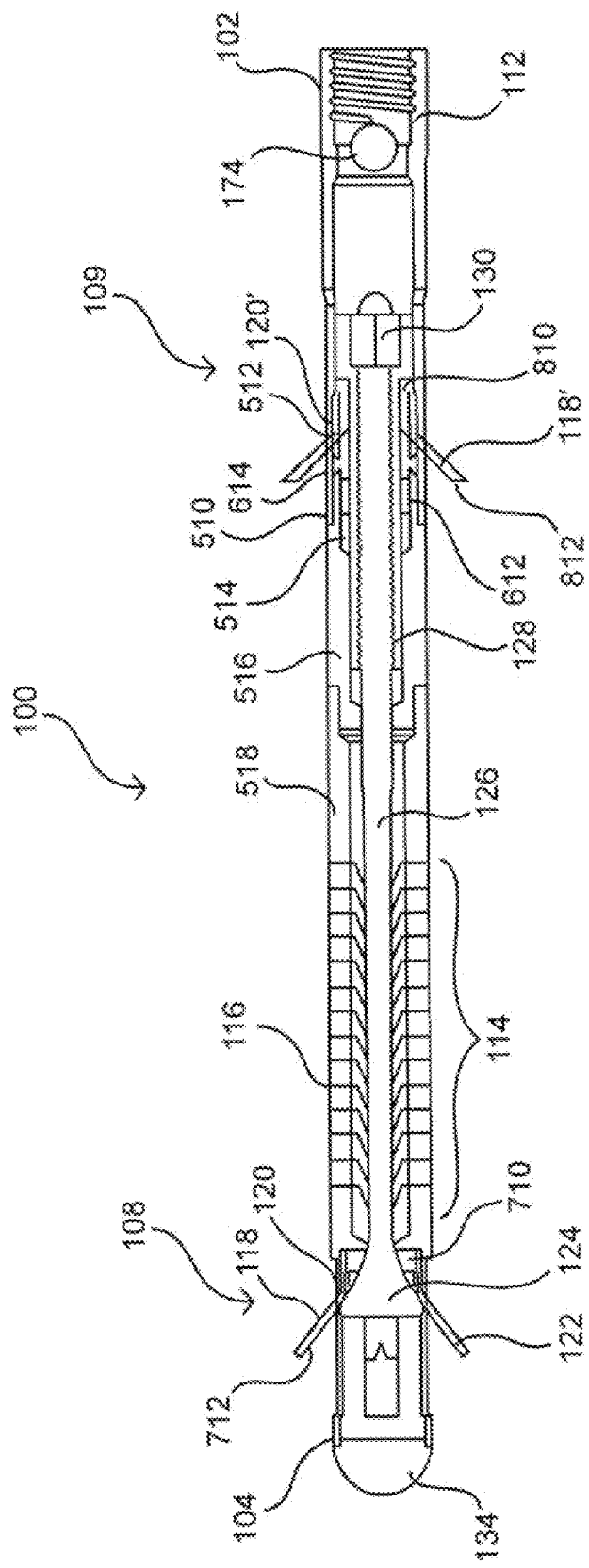
FIG. 10 is a cross-section view of the device of FIG. 3 in a deployed state.

FIGS. 9 and 10 show longitudinal cross-sections of device 100 with its components fully assembled as previously described. FIG. 9 shows device 100 in a retracted state, while FIG. 10 shows device 100 in a deployed state. To deploy grippers 108 and 109, a driver tool, such as one with a hexagonal tip (not shown) is inserted be axially into the proximal end 102 of device 100 until the tool tip is received within keyed socket 130 of drive member 128. When the driver tool is axially rotated, threadably engaged drive member 128 and actuator 126 are drawn together (i.e. drive member 128 moves left toward the distal end 104 and actuator 126 moves right toward the proximal end 102 of device 100). In alternative embodiments, a barbed, serrated wire may be used instead of actuator 126, and it may be ratcheted through a mating drive member. In an alternative embodiment, actuator 126 may be made of a super elastic alloy that when released from its insertion state it returns to its unstressed state thereby driving grippers 108 and 109 outward, shortening the device thereby compressing 518 into a rigid state.

During this actuation, bendable members 118 of proximal gripper 108 are urged radially outward by a ramped surface on actuator head 124. Actuator head 124 is formed on the distal end of actuator 126 and contacts ramped surfaces 712 on the distal ends of bendable members 118. As actuator head 124 is drawn proximally, thinned portions 120 bend and allow bendable members 118 to pivot outwardly through slots in distal body member 518. Gripper 108 and the actuator head 124 may be reversed in their geometrical layout of the device. The gripper 108 may be drawn by the actuator 126 over the actuator head 124, thereby deflecting the bendable members, 118, outward. Similarly, the bendable members, 118, may be made of a super elastic or elastic or spring alloy of metal whereby the bendable members are predisposed in their set state in the insertion configuration, that being their smallest diameter. When the actuator head, 124, engages the super elastic, elastic or spring alloy of steel bendable members 118, a continuous force is imparted upon actuator head 124 such that the bendable members 118 return to their insertion geometry after the actuator head 124 is removed. Typical super elastic, elastic, or spring alloys of metals include spring steels and NiTi or nitinol. Conversely, bendable members 118 may be made of super elastic, elastic, or spring alloys of metal and set in their maximum outside diameter, in their deployed state. Actuator 124 and the rectangular apertures in 518 would work cooperatively to expose the bendable members 118. Since the bendable members 118 would be set in their maximum outside dimension and constrained within 518, upon exposure of 118 to the rectangular apertures, the bendable members would be driven by the material properties into the bone.

At generally the same time that gripper 108 is being deployed, drive member 128 is moving distally, carrying proximal gripper 109 with it. This motion drives the ramped surfaces 812 at the end of bendable members 118' against the ramped surfaces 614 on the ends of T-shaped appendages 612 of coupling member 516, thereby urging the distal ends 122' of bendable members 118' radially outward. As gripper 109 continues to move distally, thinned portions 120' bend and allow bendable members 118' to pivot outwardly through slots in proximal body member 510. Gripper 109 and the coupling member 516 may be reversed in their geometrical layout of the device. The gripper 109 may be drawn by the drive member 128 over the coupling member 516, thereby deflecting the bendable members, 118', outward. Similarly, the bendable members, 118', may be made of a super elastic or elastic or spring alloy of metal where by the bendable members are predisposed in their set state in the insertion configuration, that being their smallest diameter. When the coupling member 516, engages the super elastic, elastic or spring alloy of steel bendable members, 118', a continuous force is imparted upon coupling member 516 such that the bendable members 118, return to their insertion geometry after the coupling member 516 is removed. Typical super elastic, elastic, or spring alloys of metals include spring steels and NiTi or nitinol. Conversely, bendable members 118' may be made of super elastic, elastic, or spring alloys of metal and set in their maximum outside diameter, in their deployed state. Coupling member 516 and the rectangular apertures in 510 would work cooperatively to expose the bendable members 118'. Since the bendable members 118' would be set in their maximum outside dimension and constrained within 510, upon exposure of 118' to the rectangular apertures, the bendable members would be driven by the material properties into the bone.

It can be seen in FIG. 9 that bushing 514 initially prevents T-shaped appendages 612 from collapsing radially inward. However, as drive member 128 carries bushing 514 far enough toward distal end 104, bushing 514 lines up with the circumferential portions of T-shaped slots 610 (shown in FIGS. 6A and 6B) and the necked down portions 616 of T-shaped appendages 612. Once bushing 514 has advanced this far distally, T-shaped appendages 612 are permitted to bend at necked down portions 616 and collapse radially inward as gripper 109 continues to advance distally. An advantage to this arrangement is that is allows grippers 108 and 109 to initially anchor themselves within the intramedullary cavity of the bone before T-shaped appendages 612 are permitted to collapse. Further rotation of drive member 128 allows bendable members 118' to further advance in the distal direction (by collapsing T-shaped appendages 612) rather than being forced to continue to expand only in the radial direction. This two-stage action allows grippers 108 and 109 to anchor on opposite sides of a bone fracture and then move closer together to approximate the fracture.

As previously mentioned, device 100 may include one or more flexible-to-rigid body portions 114. This feature is flexible upon entry into bone and rigid upon application of compressive axial force provided by tensioning actuator 126. Various embodiments may be used, including dual helical springs whose inner and outer tubular components coil in opposite directions, a chain of ball bearings with flats or roughened surfaces, a chain of cylinders with flats, features, cones, spherical or pointed interdigitating surfaces, wavy-helical cut tubes, two helical cut tubes in opposite directions, linear wires with interdigitating coils, and bellows-like structures. The flexible to rigid bodies may have a polygonal cross sectional geometry having any suitable number of sides from 1 to infinity. The flexible-to-rigid body may be cut in a specific way so that upon activation it conforms to a specific shape. The resultant shape may resemble or match the original anatomical shape of the bone. The resultant shape may provide specific translational actions so as to improve the healing of bone or create a resultant bone-implant construct that promotes a desired resultant geometry or effect. These resultant geometries may be bone lengthening where growth of the bone is improper, bone rotation to remediate poor pronation, supination, deflection, extension, deviation, or inclination of an appendage or joint. The shape of the flexible-to-rigid body may be devised or designed from x-ray or CT scans of the contralateral unaffected anatomy to return the affected anatomy to its original anatomical configuration or match the existing contralateral configuration.

Figure 16:
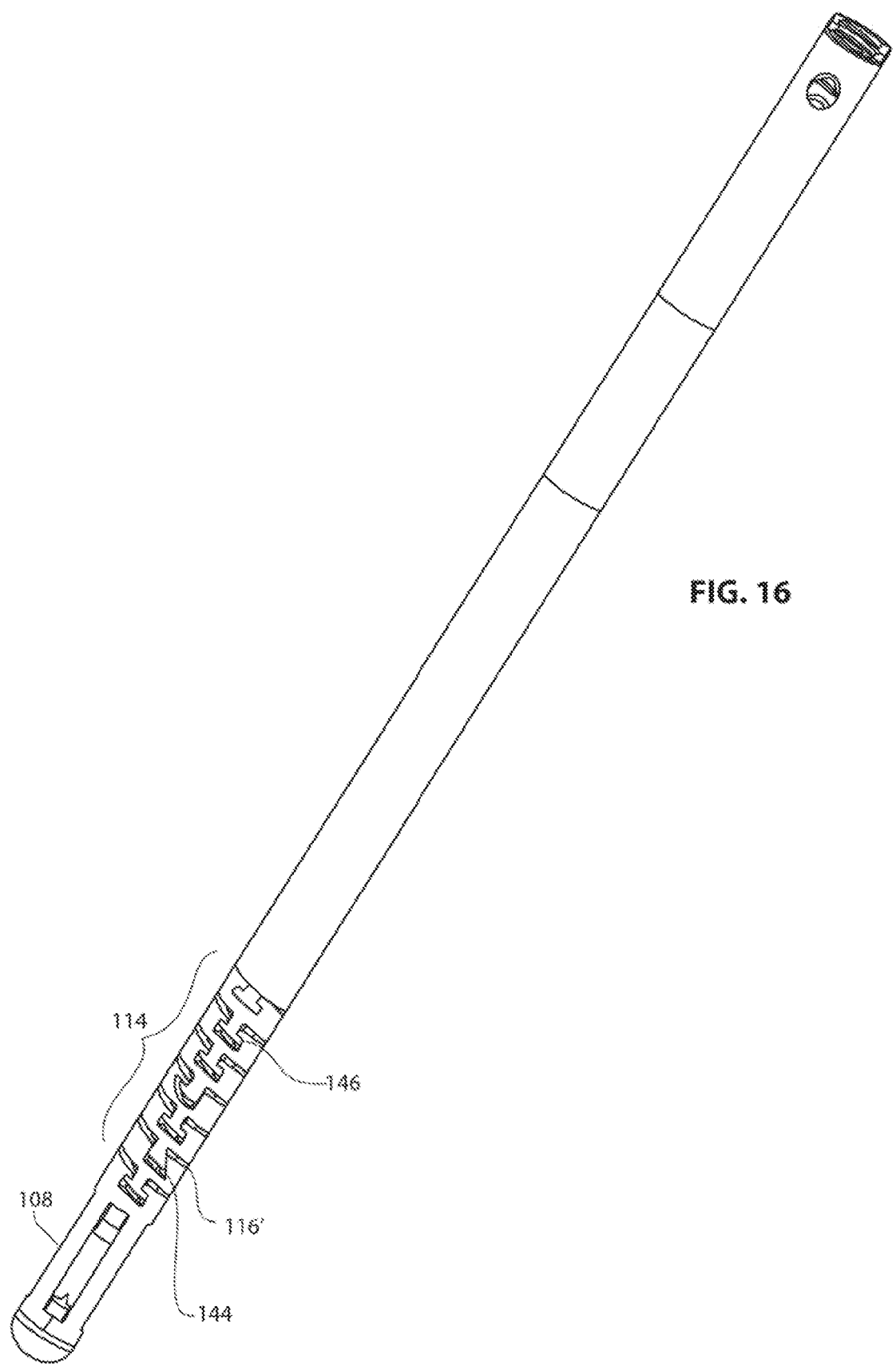
FIG. 16 is a side view of an alternative embodiment.

The design of the flexible-to-rigid tubular body portion 114 allows a single-piece design to maximize the transformation of the same body from a very flexible member that minimizes strength in bending to a rigid body that maximizes strength in bending and torque. The flexible member transforms to a rigid member when compressive forces are applied in the axial direction at each end, such as by an actuator. The body portion 114 is made, for example as shown in FIG. 3, by a near-helical cut 116 on a tubular member at an angle of incidence to the axis somewhere between 0 and 180 degrees from the longitudinal axis of the tubular body portion 114. The near-helical cut or wavy-helical cut may be formed by the superposition of a helical curve added to a cyclic curve that produces waves of frequencies equal or greater than zero per turn around the circumference and with cyclic amplitude greater than zero. The waves of one segment nest with those on either side of it, thus increasing the torque, bending strength and stiffness of the tubular body when subjective to compressive forces. The tapered surfaces formed by the incident angle allow each turn to overlap with the segment on either side of it, thus increasing the bending strength when the body is in compression. Additionally, the cuts can be altered in depth and distance between the cuts (i.e. thickness) on the longitudinal axis along the length of body portion 114 to variably alter the flexible-to-rigid characteristics of the tubular body along its length. As shown in FIG. 15 or 16 for example, the body portion 114 is made by a patterned cut 116'. The pattern may be a repeating pattern, or it may be a non repeating pattern as shown in the Figures. As shown in FIG. 16, the patterned cut 116' may include a ramp 142, edges 144, and inter-digitations 146 (i.e. portions that are interlocking). The ramp 142 may function to dictate the radius of curvature and/or the chord length of the geometry of the elongate body in its rigid state. The ramp may be sized and configured such that the geometry in the rigid shape fits or matches the anatomical curvature of the specific bone into which it will be implanted. The edges 144 may function to prevent axial displacement or excessive elongation of the elongate body. The edges may function to prevent the elongate body from unraveling and allow for the removal of the device. In some embodiments, the edges may be sized and configured to withstand up to about 200 pounds-force. The inter-digitations 146 may also function to prevent axial displacement or excessive elongation of the elongate body and in some instances, they may provide torsional resistance, especially when the elongate body is curved and in a rigid state.

The cuts 116 in body portion 114 allow an otherwise rigid member to increase its flexibility to a large degree during deployment. The tubular member can have constant or varying internal and external diameters. This design reduces the number of parts of the flexible-to-rigid body portion of the device and allows insertion and extraction of the device through a curved entry port in the bone while maximizing its rigidity once inserted. Application and removal of compressive forces provided by a parallel member such as wire(s), tension ribbons, a sheath, or actuator 126 as shown will transform the body from flexible to rigid and vice versa.

In operation, as actuator 126 is tightened, gripper members 118 and 118' are extended radially outwardly. Once the distal ends of gripper members 118 contact bone and stop moving outward, continued rotation of actuator 126 draws grippers 108 and 109 together, as previously described, and also draws the proximal end 102 and the distal end 104 of device 100 closer together until cuts 116 are substantially closed. As this happens, body portion 114 changes from being flexible to rigid to better secure the bone fracture(s), as will be further described below. Rotating actuator 126 in the opposite direction causes body portion 114 to change from a rigid to a flexible state, such as for removing device 100 if needed in the initial procedure or during a subsequent procedure after the bone fracture(s) have partially or completely healed. Body portion 114 may be provided with a solid longitudinal portion 136 (as best seen in FIGS. 3 and 4) such that cuts 116 are a series of individual cuts each traversing less than 360 degrees in circumference, rather than a single, continuous helical cut. This solid portion 136 can aid in removal of device 100 by keeping body portion 114 from undesirably extending like a spring.

If removal of device 100 is desired, keeper ring 512 also serves to help retract gripper 109. Keeper ring 512 pulls gripper 109 in the proximal direction as drive member 128 moves proximally, and also as device 100 is being withdrawn, to keep gripper 109 from sliding distally along drive member 128. With drive member 128 retracted to its original proximal position and actuator 126 extended to its original distal position (as both shown in FIG. 9), bendable gripper members 118, 118' are free to retract back within distal body member 518 and proximal body member 510, respectively, as device 100 is withdrawn from the bone in the proximal direction.

As shown in FIGS. 9 and 10, hub 112 at the proximal end 102 of device 100 may be provided with an angled hole 174 for receiving a bone screw, interlocking pin, or transverse bone attachment member to further anchor device 100 to a bone, as will be later described. Hole 174 may be tapped to interfere with the bone screw, interlocking pin, or transverse bone attachment member so that there is mechanical interference between the hub 112 and the attachment member, such that, over time, the attachment member does not back out or translate away or into the hub unexpectedly. Hub 112 may also be provided with an internally threaded bore as shown. This threaded bore can serve to attach an insertion and removal tool (not shown) to aid in placing or removing device 100 in the intramedullary space of a bone. A step may also be provided at the proximal end of hub 112 to mate with a similar step of the insertion tool to prevent device 100 from rotating with respect to the tool. The step can be semicircular or of any suitable geometrical configuration so that the insertion tool and hub are keyed relative to each other for alignment and secure positioning. After disengaging the tool from device 100, the threaded bore may also serve to receive an end plug (not shown) to prevent ingrowth of tissue into implanted device 100.

Figure 11:
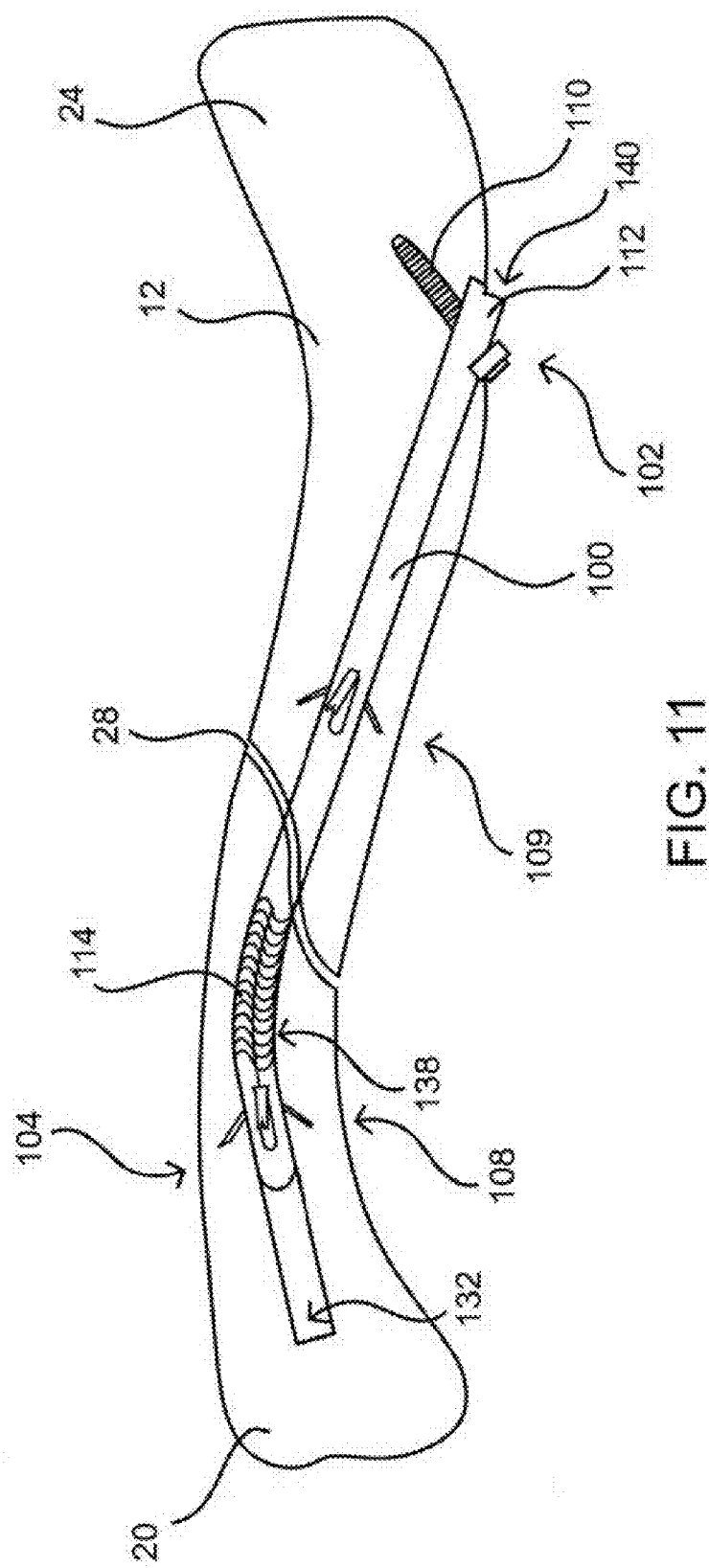
FIG. 11 is a superior view showing the device of FIG. 3 implanted in a right clavicle.
Figure 12:
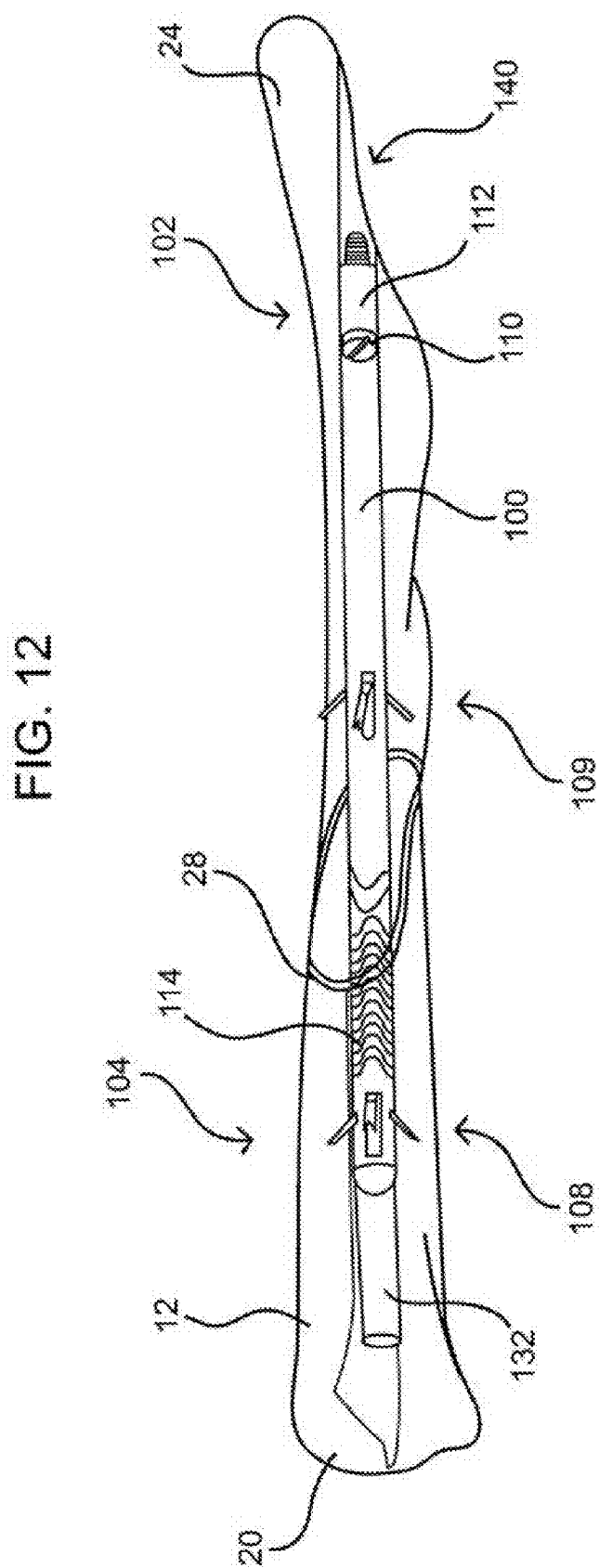
FIG. 12 is a posterior view showing the device of FIG. 3 implanted in a right clavicle.

FIGS. 11 and 12 show device 100 implanted in a right clavicle 12. FIG. 11 shows clavicle 12 from a superior perspective, while FIG. 12 shows clavicle 12 from a posterior perspective. As shown, the clavicle has a lateral segment having a lateral end 24 and a medial segment having a medial end 20. In a patient, the lateral end is adjacent to the acromion of a scapula and the medial end is adjacent to the manubrium of a sternum. As shown in FIGS. 11 and 12, the lateral segment is between the fracture 28 and the lateral end 24 and the medial segment is between the fracture and the medial end 20.

A method of implanting the device 100 into a bone and of repairing the bone, such as a clavicle, may include the steps of creating an intramedullary channel 132 and inserting the bone fixation device into the channel. The channel may be created such that the channel traverses the fracture 28 of the bone and comprises at least one segment 138 that substantially follows the anatomical contour of the bone. The bone fixation device may be inserted into the channel such that the device traverses the fracture and at least a portion 114 of an elongate body of the fixation device in a flexible state is placed within the contoured segment of the channel. The method may further comprise the step of operating an actuator to deploy at least one gripper of the fixation device to engage an inner surface of the intramedullary channel to anchor the fixation device to the clavicle.

In a first embodiment, to implant bone fixation device 100 in clavicle 12, an incision is first made at the fracture 28, and tissue is retracted if needed to access the fracture. Fracture 28 is then distracted to gain access to the medial end of the lateral portion of the bone. A channel may then be drilled axially through the lateral portion of the bone from fracture site 28 outward toward the lateral end 24 until it surfaces at the lateral end as shown. A guidewire, such as a K-wire, may first be driven anterior to posterior thereby tenting the posterior skin and the drill guided over the guidewire anterior to posterior in the lateral clavicle segment.

A second incision may be made where the channel exits lateral end 24 of clavicle 12 in order to access the exit point. A guide wire may then be placed through the second incision and into the lateral exit point of the channel created in the lateral portion of clavicle 12. The guide wire may then be fed medially through the channel to the fracture site 28. With the fracture approximated, the guide wire may be advanced across the fracture site and into the medial portion of clavicle 12. Note that the path of the guide wire may need to bend to approximately follow the longitudinal axis of clavicle 12. The procedure may be done under fluoroscopy or other imaging technique to allow the surgeon to visualize the path of the guide wire as it is advanced, and/or to confirm its location once extended through clavicle 12. A guiding sheath or cannulated drill bit may alternatively be used to facilitate the placement of the guide wire from anterior to posterior in the lateral clavicle fragment, thereby allowing the guide wire to be passed either anterior to posterior in the lateral fragment or posterior to anterior in the lateral fragment.

A canulated drill, reamer, or other channel forming instrument may then be advanced over the guide wire to create a straight or curved channel in the medial portion of clavicle 12 as needed. Once the desired intramedullary channel is created on both sides of fracture 28, device 100 may be inserted into the channel through the lateral exit point.

As previously described, grippers 108 and 109 are in a retracted state during insertion, and flexible to rigid body portion 114 is in a flexible state. With fracture 28 roughly approximated, grippers 108, 109 may be deployed and body portion 114 converted to a rigid state by inserting a rotary drive tool through the second incision and into proximal end 102 of device 100, and rotating the tool as previously described. According to aspects of the invention, this action can further approximate fracture 28. One or more screws 110 may be inserted in the second incision and through hub 112 as shown to further secure proximal end 102 of device 100 to the lateral end 24 of clavicle 12. At this point, any insertion tool attached to device 100 may be removed and replaced with an end plug if desired, and the incisions are closed.

In a second embodiment, to implant bone fixation device 100 in clavicle 12, an incision is first made at the fracture 28. The patient may be positioned in the "beach chair" position or any other suitable position for surgery. The incision is made at the front (anterior side) of the patient adjacent to the fracture. Tissue is retracted if needed to access the fracture and the fracture 28 may then be distracted or elevated to gain access to each of the segments of the bone. The medial segment and lateral segment are then both prepared for the insertion of the device by creating a channel within them.

Any suitable combination of tools may be used to create the channels in both the medial segment and the lateral segment of the clavicle. The tools may include hand tools or power tools. The tools may also include awls, drill bits, guidewires, or any other suitable tools to create a channel within bone. The awls may be curved awls, straight awls, and/or malleable awls (i.e. the user may change the radius of curvature of the awl intraoperatively). The tools may have any suitable head geometry such as a pointed geometry, a blunted geometry, a fluted geometry, etc. In some cases, a blunted tip is preferably over a sharp tip as to avoid important nerves (such as the bracheoplexus) and vessels (such as the subclavian artery which supplies blood to the brain) that surround the clavicle bone. The tools may be cannulated (i.e. hollow) or solid. In the case that the tool is cannulated, it may be adapted to be inserted into the bone over a guidewire and/or the tool may function as a sheath or trocar like device and a guidewire may be inserted through the cannula of the cannulated tool.

The segments may be prepared in any suitable order. As an example, the medial segment may be prepared first. The channel is created in the medial segment by inserting a tool into the medial segment starting at the fractured end. The tool is then moved through the medial segment creating the channel. The channel substantially follows the anatomical contour of the bone. In the case of the clavicle, as shown in FIG. 11, this means following the curve of the bone through the medial segment. A curved tool may be used to create the curved or contoured segment of the channel. A straight tool may be used to create the substantially straight segments before and/or after the curved or contoured segment. As shown in FIG. 12, the channel 132 is created substantially along the midline of the bone. Furthermore, the channel 132 may run deeper into the medial segment of the bone than conventional channels can because it is a curved channel. Conventional channels cannot be curved, and therefore they cannot be created past the curved portion or bend in the medial segment of the clavicle bone without breaking out of the bone.

As an example, once the medial segment is prepared, the lateral segment may be prepared by creating a channel through the lateral segment of the clavicle. The channel is created in the lateral segment by inserting a tool into the lateral segment starting at the fractured end. The tool is then moved through the lateral segment creating the channel. As shown in FIG. 11, the channel through the lateral segment may be substantially straight, and may exit the lateral segment of the clavicle toward the lateral end 24 of the bone, creating a port 140 through which other tools and/or the device can be inserted. As shown in FIG. 12, the channel 132 is created substantially along the midline of the bone.

As described above, any suitable combination of tools may be used to prepare the medial segment and then the lateral segment. For example, a smaller diameter channel may initially be created by a guidewire and/or an awl. The channel may be made larger by then inserting a larger diameter tool such as a larger awl, a drill bit, and/or a reamer. Once the initial channel is created in both the lateral and the medial segments, a guidewire may be inserted into the channels. The guidewire may be inserted through the incision such that a first end is inserted into the medial segment, and then a second end is inserted into the lateral segment. The second end may be inserted through the lateral segment such that it exits the bone at the port 140. The guidewire may then "tent" or raise the skin of the patient at their back as the guidewire passes out of the bone. The guidewire may be used to puncture the skin at this point, or an additional incision may be made in the back of the patient, adjacent to the port at the lateral end of the bone. Alternatively, the incision at the back of the patient may be made first (or the guidewire may puncture the skin) and the guidewire may be inserted from the back of the patient, through the port, into the lateral segment of the bone, across the fracture, and into the medial segment of the bone. The fracture may be reduced (i.e. brought together) before or after the insertion of the guidewire. The fracture may be held together with conventional surgical bone clamps.

Once the guidewire is in place within the channel 132, tools may be inserted into the channel over the guidewire. For example, a cannulated reamer (stiff and/or flexible) or cannulated drill bit may be inserted through port 140 and into the clavicle by being threaded over the guidewire. A straight tool may be used to enlarge the diameter of the straight portions of the channel, and a curved or flexible tool may be used to enlarge the diameter of the curved and/or straight portions of the channel. The guidewire may function to guide the tools through the bone such that the tools follow the anatomical curvature of the bone (through at least a portion the medial segment), and stay substantially at the midline of the bone. In some instances, the initial channel of lateral segment will have a larger diameter than the initial channel of the medial segment, so tools may be used to only enlarge a portion (e.g. the medial segment) of the channel.

Figure 24:
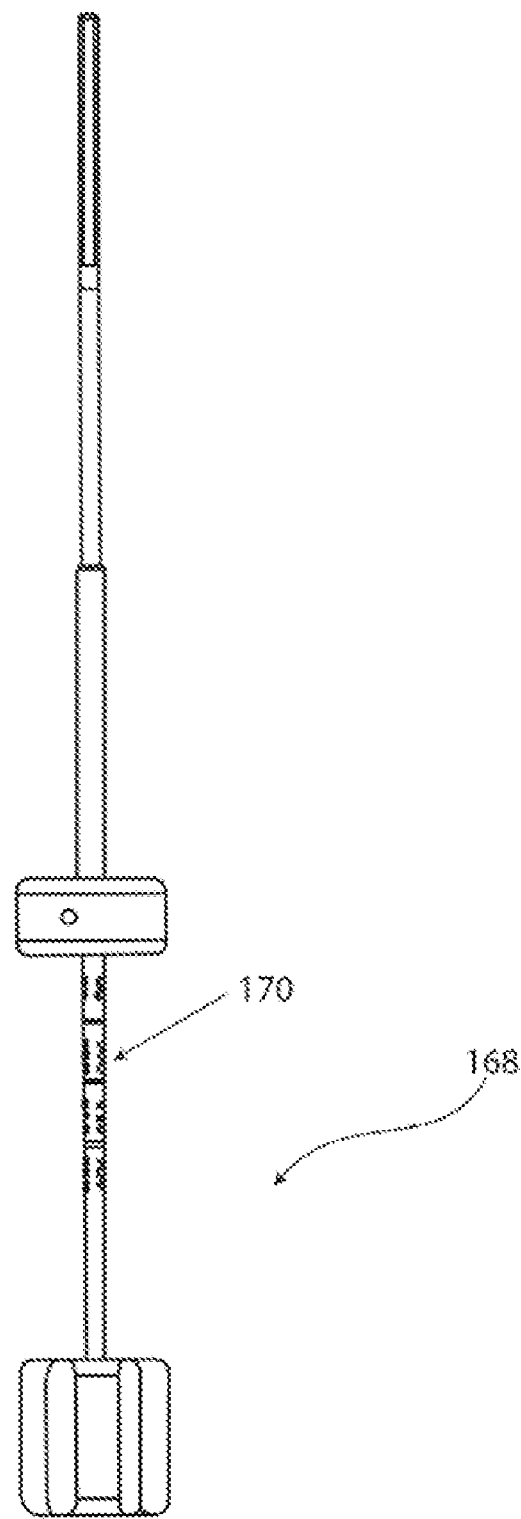
FIG. 24 is a side view of an embodiment of a depth gauge.

Additional tools may be inserted into the channel over the guidewire. For example, a depth gauge 168, as shown in FIG. 24, may be inserted into the channel. In some embodiments, the depth gauge includes markings 170 to indicate the depth of the channel created. The markings may be reverse scale markings such that the deeper that the gauge can be inserted into the channel, the higher the marking that will be legible. The depth reading may be used to determine the length of device needed to fit correctly within the channel. The flexible to rigid body portion 114 may rest substantially within the contoured portion 138 of the channel and the end of the device is just below the outer surface of the bone. Various lengths and diameters of devices may be provided for the surgeon to select from to suit the particular anatomy and fracture involved. For example, device 100 may be provided in 4, 5 and 6 mm diameters, and in 50, 75, 100 and 125 mm lengths. Dimensions and configurations can be altered for use in bones other than the clavicle.

Figure 25:
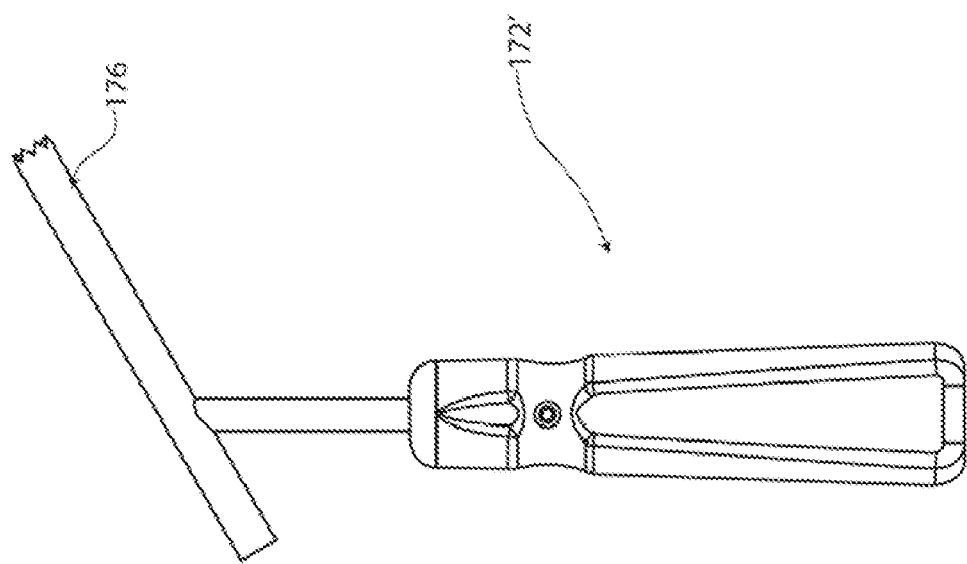
FIG. 25 is a side view of a first embodiment of a protection tool.
Figure 26:
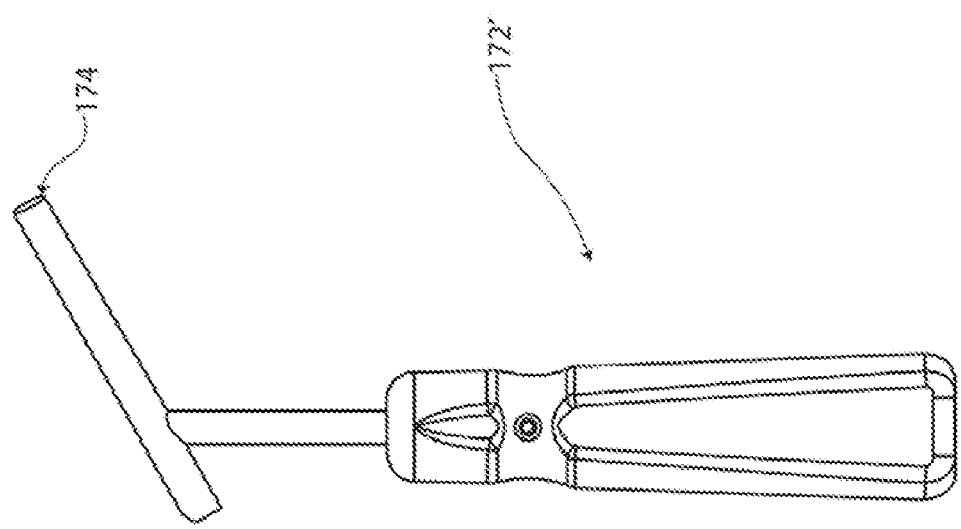
FIGS. 26 and 27 are a side view and an exploded view, respectively, of a second embodiment of a protection tool.
Figure 27:
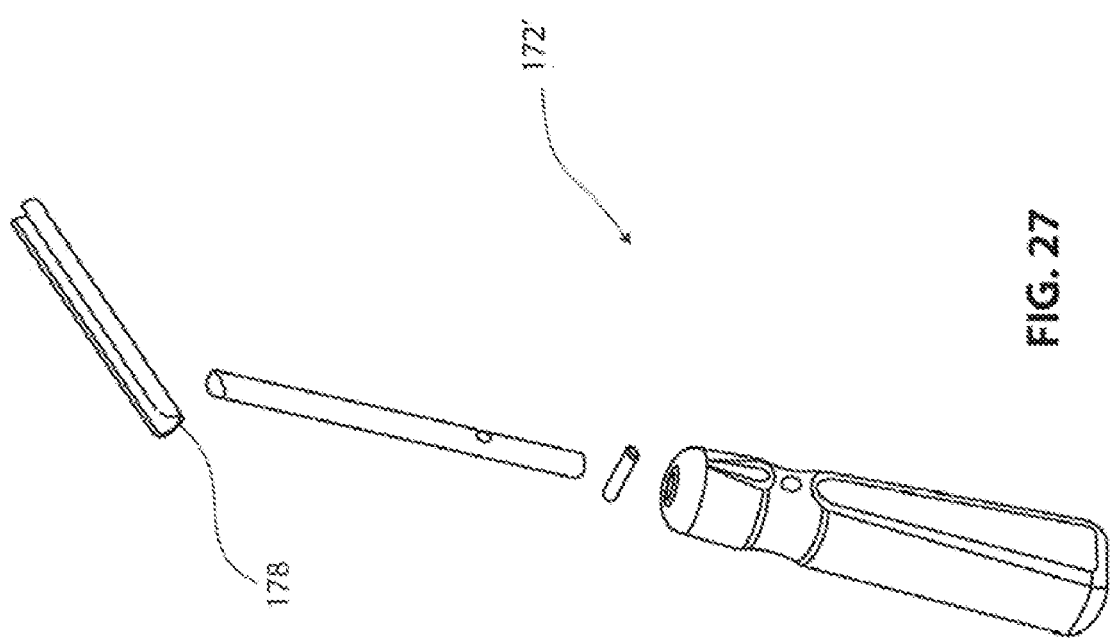

The device may then be inserted through the port 140 and positioned within the intramedullary channel 132, as shown in FIGS. 11 and 12. In order to insert the device through the incision and the surrounding soft tissues, a tissue protection tool may be used. As shown in FIGS. 25-27, the tissue protection tool 172 or 172' may function to guide the device through the soft tissue to the port while protecting the soft tissue from being damaged by the device. In some embodiments, as shown in FIGS. 26 and 27, the protection tool comprises a tapered portion 174 at one end of the tool. The tapered portion may be sized and configured to fit at least partially within the entry port in the bone. The tapered portion may function to pilot or guide the fixation device into the channel in the bone. As shown in FIG. 25, the protection tool comprises a toothed portion 176 at one end of the tool. The toothed portion may be sized and configured to fit at least partially within the entry port in the bone or may alternatively be sized and configured to grip the end of the bone. In some embodiments, as shown in FIG. 27, the protection tool has a U-shaped cross section 178 that cradles the fixation device. Once the fixation device is in place and/or at least partially within the channel of the bone, the protection tool may simply be pulled off of the fixation device. In some embodiments, the fixation device may be sold or provided to a user already coupled to the protection tool. Alternatively, the protection tool may be sold or provided to a user coupled to a combination tool or other insertion, actuation, and/or alignment devices. The combination tool and insertion, actuation, and/or alignment devices are described in further detail in U.S. Provisional Application 61/060,445, filed 10 Jun. 2008. Once inserted, the device may be actuated to anchor the fixation device to the bone, as described above.

In an alternative method, the entire implant procedure may be performed through a single incision at the lateral end 24 of clavicle 12. In this alternative procedure, a drill enters the lateral portion of clavicle 12 and is advanced to fracture site 28. A guide wire may then be advanced across the approximated fracture site and into the medial portion of the bone. A canulated drill or reamer may then be advanced over the guide wire to complete the intramedullary channel in the medial portion of clavicle 12. Device 100 is then inserted and deployed and described above. This alternative method may be referred to as a "closed" procedure and requires more work and skill to perform, but is less invasive than the first method described. In any method, it is envisioned that the use of a guide wire may be omitted if desired, particularly if device 100 is deployed in a relatively straight portion of bone.

In an alternative variation of the "closed" procedure, once an incision is made adjacent to an end portion of the lateral segment of the clavicle, the channel may be created in a clavicle bone by inserting a tool or a series of tools through the incision and into the end portion of the lateral segment of the of the clavicle. As described above, a tool is inserted into the bone and advanced through the bone such that it traverses the fracture of the bone. The tool may be a guidewire. The guidewire has a stiffness such that it may traverse the fracture. For example, a guidewire with adequate stiffness to traverse the fracture may be one that is stiff enough to maintain a substantially straight trajectory through the midline of the bone, and one that will not buckle or otherwise bend or fail within the bone or across the fracture. Once a tool has been inserted into the bone and across the fracture, a second tool may be inserted to create the medial segment of the channel. The channel within the medial segment of the clavicle substantially follows the anatomical curvature or contour of the clavicle bone. Any suitable tool may be used to create this contoured segment of the channel. For example, a second guidewire may be inserted (in some cases, after the first guidewire is removed) into the clavicle at the lateral end and moved through the bone, following the anatomical curvature of the bone. The second guidewire is less stiff than the first guidewire such that it may flex and bend around the curvature of the clavicle and create an anatomically matching (i.e. curved) channel within the bone. Any number of guidewires having any combination of stiffnesses may be used sequentially to create the channel within the clavicle such that at least a portion of the channel matches the anatomical contour of the clavicle.

In an alternative example, a cannulated reaming tool or drill bit may be advanced into the bone over one of the guidewires described above. The cannulated tool may be used to expand the diameter of the channel to a diameter large enough to accept the fixation device. The cannulated tool may be stiff or flexible. For example, if the tool is flexible, it may be advanced over the guidewire and follow the curve of the channel to create a contoured and anatomically matching channel. The cannulated tool may also function as a sheath or trocar-like device. For example, the cannulated tool may remain at least partially within the bone, and one or a series of guidewires may be inserted and removed through the cannulated tool. Alternatively, the guidewire may be removed, and a tool (cannulated or not) may be moved through the bone independently.

Figure 13:
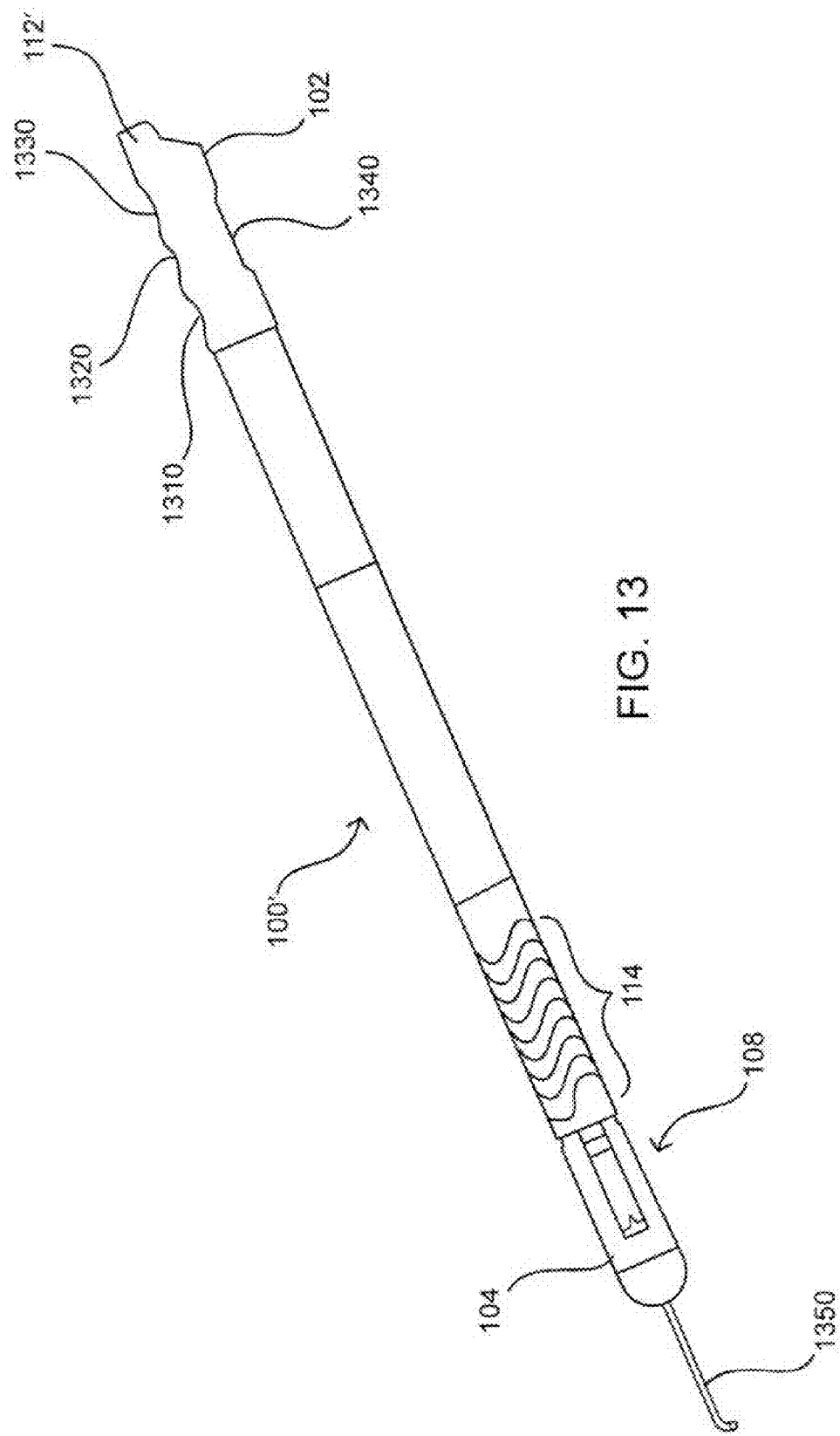
FIG. 13 is a side view of an alternative embodiment.
Figure 14:
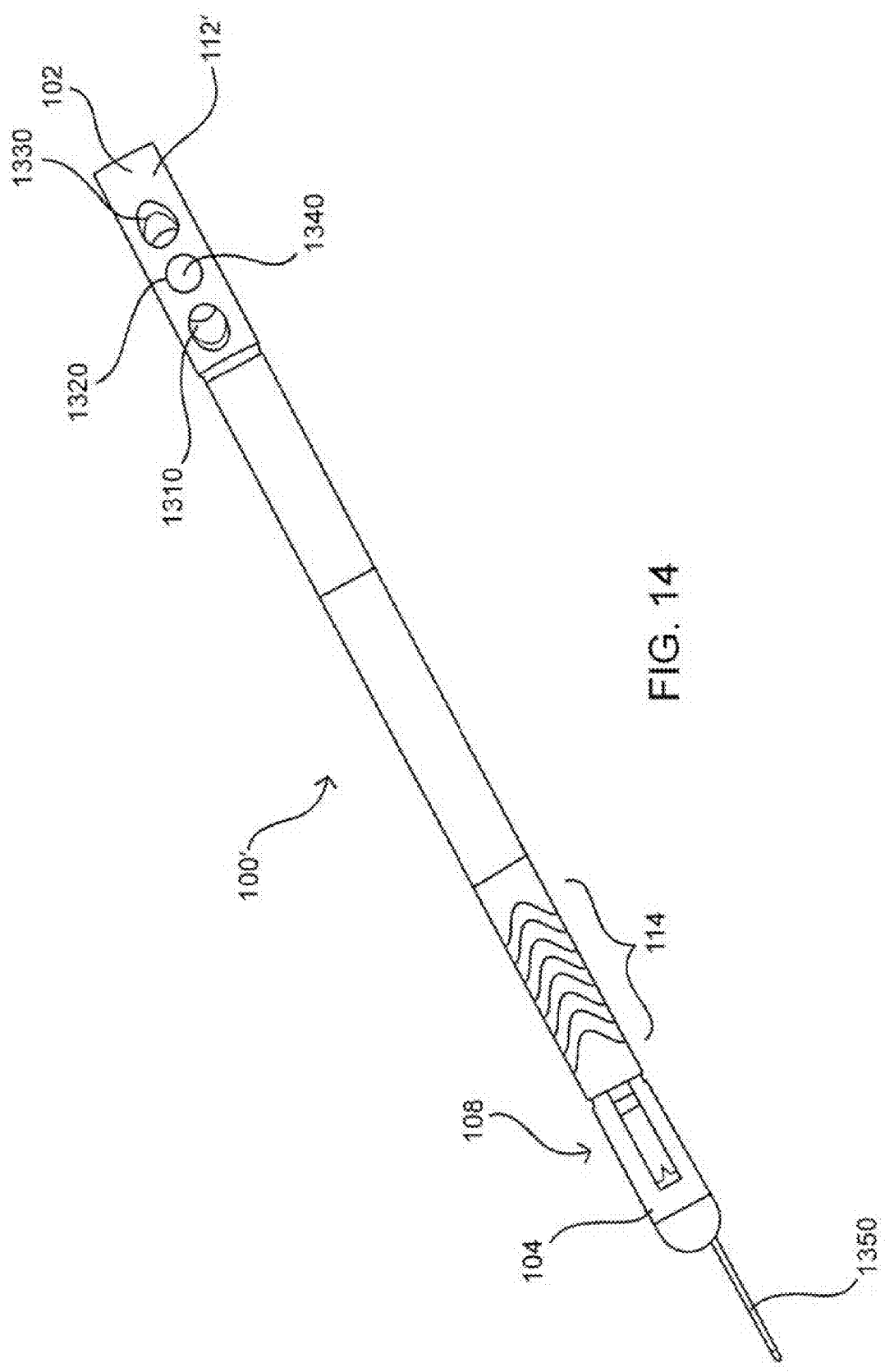
FIG. 14 is a top view of an alternative embodiment.

FIGS. 13 and 14 show an alternative embodiment similar to device 100 described above. Device 100' includes a distal gripper 108 but does not include a proximal gripper. The proximal end 102 of device 100' is secured to the bone by one or more bone screws. For this purpose, three through holes 1310, 1320 and 1330 are provided in hub 112' at various angles. Hole 1320 runs perpendicularly to hub 112, and holes 1310 and 1330 on either side angle toward hole 1320. The three holes share a common exit point, which is an elongated slot 1340 on the opposite side of hub 112. FIG. 16, shown an embodiment similar to that of FIGS. 13 and 14 that includes a patterned cut 116' as described above.

Figure 18:
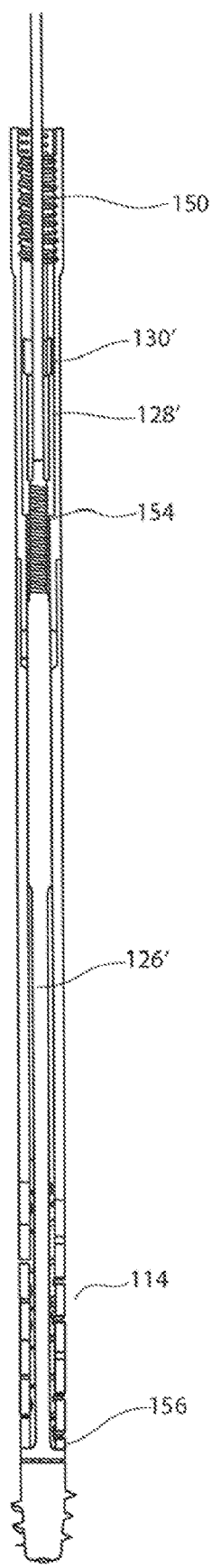

FIGS. 17 and 18 show another alternative embodiment similar to device 100 described above. Device 1700 further includes a screw tip 148. The screw tip may be sized and configured to screw into bone. Additionally, the screw tip may be sized and configured to be a self tapping screw tip. In some variations, as shown in FIG. 17, the device 1700 may not need to include distal and/or proximal grippers due to the engagement of the screw tip into bone. Additionally, the flexible-to-rigid portion 114 of the elongate body may function as the actuatable bone engaging mechanism (either alone or in addition to the screw tip) by gripping the bone as the elongate body is changed from its flexible state to its rigid state. In some embodiments, a channel is created in the bone prior to inserting device 1700. The diameter of the channel may be about the same size as the major thread diameter of screw tip 148, or may be about the same size as the minor diameter of screw tip 148. In some embodiments, a proximal portion of the channel may be at least as large as the major diameter and a distal portion of the channel may be about the same size as the minor diameter. In other embodiments, little or no channel formation may be performed before inserting device 1700 into the bone, relying instead on the turning screw tip 148 to form its own channel as it is screwed into the bone. In some embodiments a guide wire is advanced into the bone first and device 1700 then threaded over the guide wire.

Additionally, as shown in FIG. 18, the device may further include threads 150 along a portion of the inner diameter of the elongate body, wherein the threads are sized and configured to receive a compression screw 152 (as shown in FIG. 17). The compression screw may function to compress the device 1700 against the screw tip 148 and/or to the inside walls of the channel within the bone. The compression screw may further function to approximate a fracture within the bone, in some instances by approximating the lateral segment of the bone (coupled to the compression screw) with the medial segment of the bone (coupled to the screw tip).

FIG. 18 also shows a drive member 128' positioned proximally to the flexible-to-rigid portion 114 of the elongate body and threadably engaged (as shown by threads 154) with the actuator 126'. As shown, the actuator is disposed along the length of the device, and has a surface 156 that couples to the distal end of the flexible-to-rigid portion 114. To actuate the device, as an example, a driver tool, such as one with a hexagonal tip (not shown) may be inserted axially into the proximal end of the device until the tool tip is received within keyed socket 130' of drive member 128'. When the driver tool is axially rotated, threadably engaged drive member and the distal end of the actuator are drawn together such that they apply a compressive force to the flexible-to-rigid portion the elongate body along the longitudinal axis thereby changing the elongate body from its flexible state to its rigid state.

Figure 20:
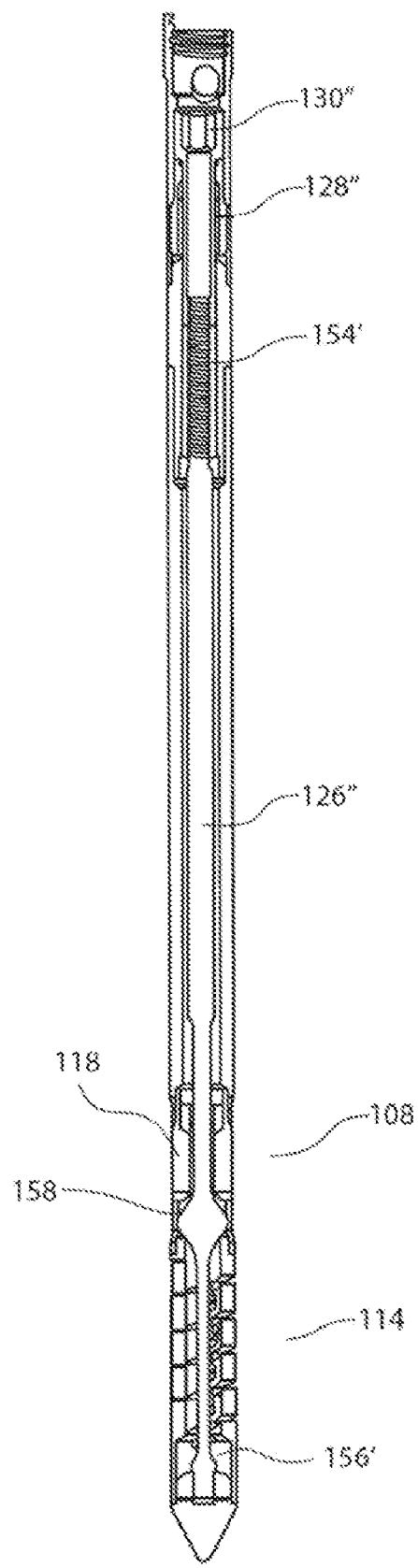

FIGS. 19 and 20 also show another alternative embodiment similar to device 100 described above. Device 1900, like device 100, includes a distal gripper 108 and a proximal gripper 109. In this embodiment, the flexible-to-rigid portion 114 of the elongate body is disposed at a location on the elongate body distal to both the distal and proximal grippers.

FIG. 20 shows a drive member 128" positioned proximally to the flexible-to-rigid portion 114 of the elongate body and threadably engaged (as shown by threads 154') with the actuator 126". As shown, the actuator is disposed along the length of the device, has a surface 156' that couples to the distal end of the flexible-to-rigid portion 114, and has a surface 158 that contacts the bendable member 118 of the first gripper 108. To actuate the device, as an example, a driver tool, such as one with a hexagonal tip (not shown) may be inserted axially into the proximal end of the device until the tool tip is received within keyed socket 130" of drive member 128". When the driver tool is axially rotated, threadably engaged drive member and actuator are drawn together. The first surface of the actuator and the drive member are drawn together thereby applying a compressive force to at least a portion of the elongate body along the longitudinal axis changing the elongate body from its flexible state to its rigid state. Additionally, the second surface moves proximally against the bendable member, thereby pivoting the bendable member of the first gripper away from the longitudinal axis.

Figure 21:
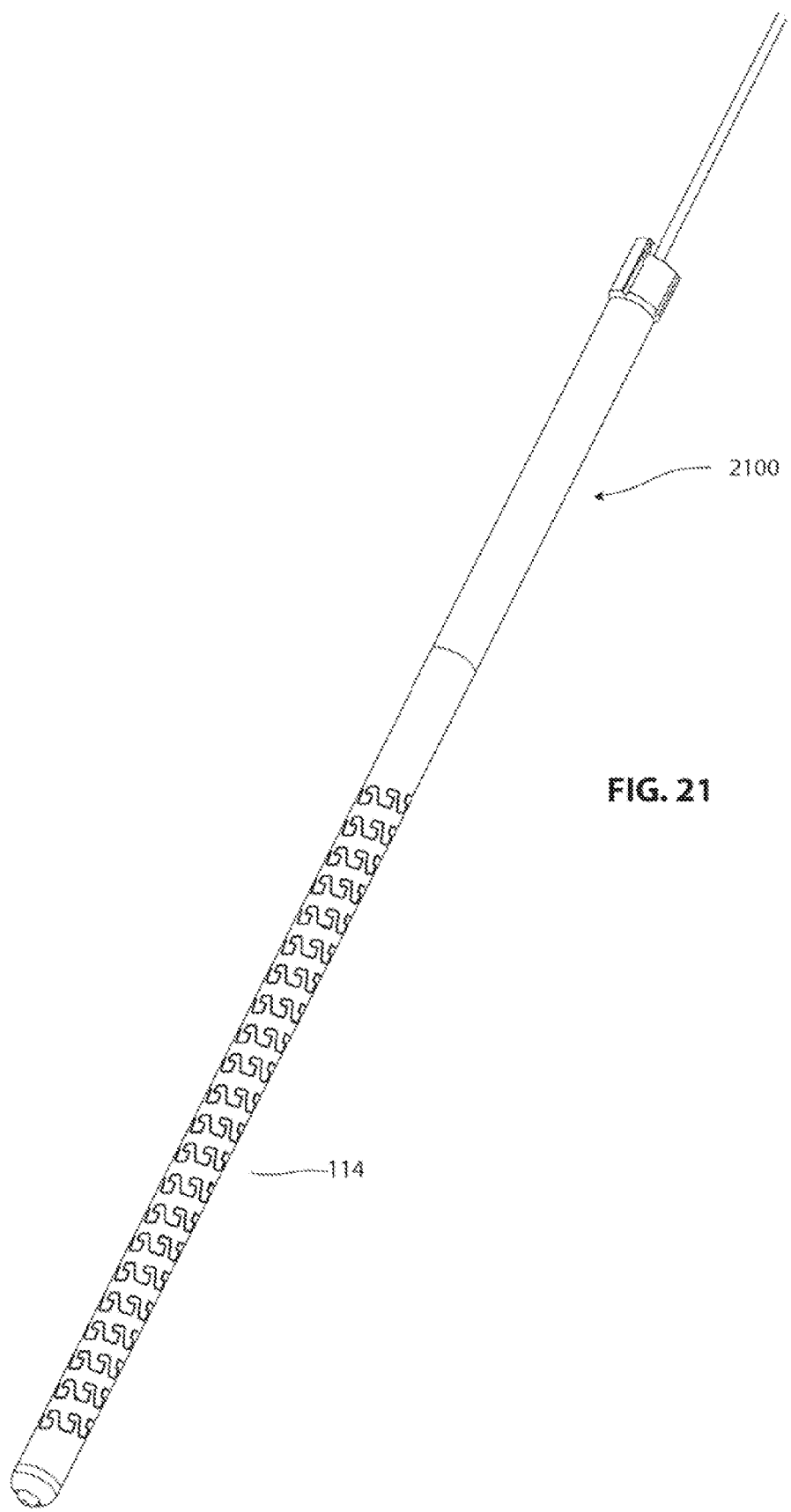
FIGS. 21-23 are a perspective view, a cross-section view, and an exploded view respectively, of an alternative embodiment.
Figure 22:
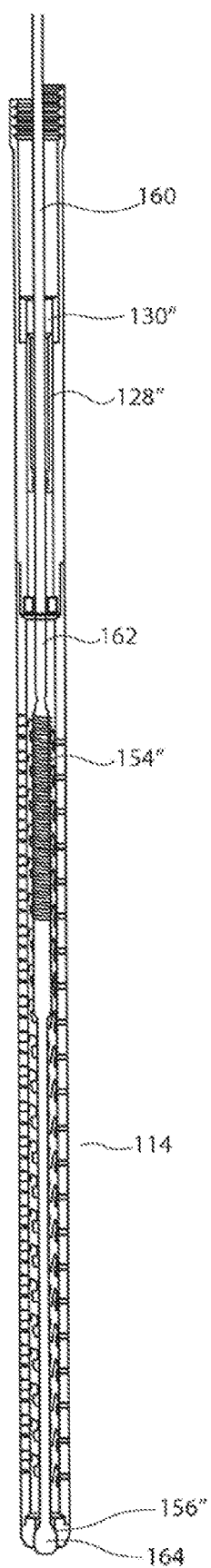
Figure 23:
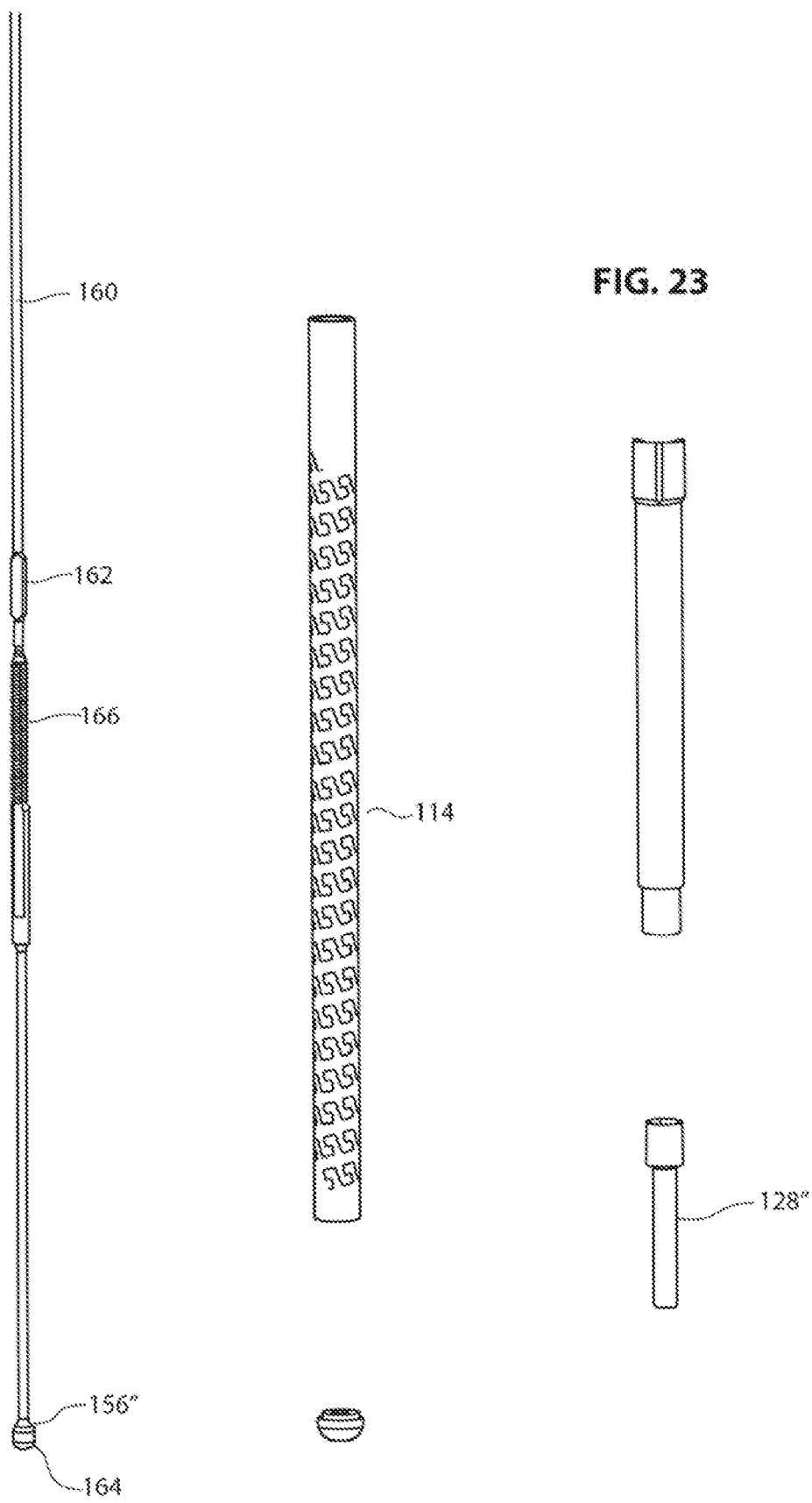

FIGS. 21-23 show yet another alternative embodiment similar to device 100 described above. Device 2100 may not include a distal gripper or a proximal gripper, but rather the flexible-to-rigid portion 114 of the elongate body may function as the actuatable bone engaging mechanism by gripping the bone as the elongate body is changed from its flexible state to its rigid state. The actuator of device 2100 is a guidewire 160. FIG. 22 shows how the elongate body is cannulated such that it is sized and configured to receive the guidewire 160. As shown, the guidewire is disposed along the length of the device. As shown best in FIG. 23, the guidewire 160 includes a distal tip 164, which includes a surface 156" that couples to the distal end of the flexible-to-rigid portion 114. The guidewire also includes features such as a threaded portion 166 and a flat portion 162. The guidewire may further include any suitable combination of features such that it may function to actuate the flexible-to-rigid portion and/or an actuatable bone engaging mechanism.

As shown in FIGS. 22 and 23, device 2100 also includes a drive member 128' positioned proximally to the flexible-to-rigid portion 114 of the elongate body and threadably engaged with the guidewire 160 (as shown by threaded portion 154" in FIG. 22). To actuate device 2100, as an example, a driver tool, such as one with a hexagonal tip (not shown) may be inserted axially into the proximal end of the device until the tool tip is received within keyed socket 130''' of drive member 128'''. When the driver tool is axially rotated, threadably engaged drive member and guidewire distal tip 164 are drawn together such that the surface 156" applies a compressive force to the flexible-to-rigid portion the elongate body along the longitudinal axis and thereby changes the elongate body from its flexible state to its rigid state.

In some embodiments, a guide wire 1350 (FIG. 13) may be used to penetrate the bone prior to inserting device 100'. A canulated reamer and/or drill can be used over the guide wire to create an intramedullary space for the device. Device 100' can then be guided into place over guide wire 1350. In other embodiments, the intramedullary space may be prepared and device 100' inserted without the use of a guidewire.

In accordance with the various embodiments of the present invention, the device may be made from a variety of materials such as metal, composite, plastic or amorphous materials, which include, but are not limited to, steel, stainless steel, cobalt chromium plated steel, titanium, nickel titanium alloy (nitinol), superelastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In a further embodiment, there is provided a low weight to volume device deployed in conjunction with other suitable materials to form a composite structure in-situ. Examples of such suitable materials may include, but are not limited to, bone cement, high density polyethylene, Kapton®, polyetheretherketone (PEEK™), and other engineering polymers.

Once deployed, the device may be electrically, thermally, or mechanically passive or active at the deployed site within the body. Thus, for example, where the device includes nitinol, the shape of the device may be dynamically modified using thermal, electrical or mechanical manipulation. For example, the nitinol device may be expanded or contracted once deployed, to move the bone or other region of the musculo-skeletal system or area of the anatomy by using one or more of thermal, electrical or mechanical approaches.

It is contemplated that the inventive implantable device, tools and methods may be used in many locations within the body. Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process(distal); on the ulna, at the head of the ulna (proximal) or the ulnar styloid process (distal); for the femur, at the greater trochanter (proximal) or the lateral epicondyle or medial epicondyle (distal); for the tibia, at the medial condyle(proximal) or the medial malleolus (distal); for the fibula, at the neck of the fibula (proximal) or the lateral malleoulus(distal); the ribs; the clavicle; the phalanges; the bones of the metacarpus; the bones of the carpus; the bones of themetatarsus; the bones of the tarsus; the sternum and other bones, the device may be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A bone fixation device comprising:
an elongate body having a longitudinal axis and a flexible-to-rigid portion, the flexible-to-rigid portion being flexible in a first state and being generally rigid in a second state which allows the elongate body to go between a flexible state and a rigid state;
an actuatable bone engaging mechanism disposed within the elongate body, wherein the bone engaging mechanism comprises a gripper having at least one bendable member such that as the gripper is actuated, the bendable member pivots away from the longitudinal axis of the elongate body and the gripper is deployed from a retracted configuration to an engaged configuration; and
an actuator operably connected to the bone engaging mechanism to actuate the bone engaging mechanism from a disengaged configuration to the engaged configuration, wherein the actuator comprises a first ramped surface that is slideably coupled to an interior surface of the bendable member of the gripper, wherein proximally moving the first ramped surface of the actuator causes the first ramped surface to slideably engage the interior surface of said bendable member at an angle thereby pivoting the bendable member of the gripper away from the longitudinal axis away from the elongate body to deploy the bone engaging mechanism into the engaged configuration.

2. The bone fixation device of claim 1 wherein the actuator is operably connected to the elongate body to change the elongate body from its flexible state to its rigid state.

3. The bone fixation device of claim 1 wherein the actuator is rotatable with respect to the bone engaging mechanism.

4. The bone fixation device of claim 1, the elongate body further comprising a drive member positioned proximally to the flexible-to-rigid portion of the elongate body and threadably engaged with the actuator.

5. The bone fixation device of claim 4 wherein the actuator, having a first interface surface, is disposed at least partially within the flexible-to-rigid portion of the elongate body such that the first interface surface is distal to the flexible-to-rigid portion of the elongate body.

6. The bone fixation device of claim 5, wherein by rotating the drive member, the first interface surface of the actuator and the drive member are drawn together thereby applying a compressive force to at least a portion of the elongate body along the longitudinal axis changing the elongate body from its flexible state to its rigid state.

7. The bone fixation device of claim 1 wherein the elongate body changes from its flexible state to its rigid state when a compressive force is applied to at least a portion of the elongate body along the longitudinal axis.

8. The bone fixation device of claim 1 wherein the flexible-to-rigid portion of the elongate body defines at least one cut having a thickness that is disposed at least partially around the circumference of the elongate body, and wherein the elongate body changes from its flexible state to its rigid state when the thickness of at least a portion of the cut is reduced.

9. The bone fixation device of claim 1 wherein the flexible-to-rigid portion of the elongate body is disposed at a location on the elongate body proximal to the bone engaging mechanism.

10. The bone fixation device of claim 1 wherein the flexible-to-rigid portion of the elongate body is disposed at a location on the elongate body distal to the bone engaging mechanism.

11. The bone fixation device of claim 1, wherein the actuator is a guidewire and the elongate body defines a cannula, wherein the cannula is sized and configured to receive the guidewire.

12. The bone fixation device of claim 11, wherein the guidewire comprises a first guidewire surface at the distal end of the guidewire and the guidewire is disposed at least partially within the flexible-to-rigid portion of the elongate body such that the first guidewire surface is distal to the flexible-to-rigid portion of the elongate body.

13. The bone fixation device of claim 12, the elongate body further comprising a drive member positioned proximally to the flexible-to-rigid portion of the elongate body and threadably engaged with the guidewire.

14. The bone fixation device of claim 13, wherein by rotating the drive member, the first guidewire surface and the drive member are drawn together thereby applying a compressive force to at least a portion of the elongate body along the longitudinal axis changing the elongate body from its flexible state to its rigid state.

15. The bone fixation device of claim 1 wherein the gripper comprises more than one bendable member, such that as the gripper is actuated each member pivots away from the longitudinal axis.

16. The bone fixation device of claim 1, the elongate body further comprising a drive member positioned proximally to the gripper and threadably engaged with the actuator.

17. The bone fixation device of claim 16, wherein by rotating the drive member, the first ramped surface of the actuator and the drive member are drawn together, such that the first ramped surface moves against the bendable member thereby pivoting the bendable member of the gripper away from the longitudinal axis.

18. The bone fixation device of claim 1,
wherein the gripper is a first gripper disposed at a distal location within the elongate body, and
the bone engaging mechanism further comprising a second gripper, the second gripper is disposed at a proximal location within the elongate body,
wherein the second gripper comprises at least one bendable member, the bendable member of the second gripper pivoting outside and away from the longitudinal axis of the elongate body when the second gripper is actuated.

19. The bone fixation device of claim 18, the elongate body further comprising a drive member and a second interface surface, wherein the drive member is coupled to the second gripper and the second interface surface is positioned distally to the second gripper.

20. The bone fixation device of claim 19, wherein by rotating the drive member a first distance the drive member moves the second gripper against the second interface surface, thereby pivoting the bendable member of the second gripper away from the longitudinal axis.

21. The bone fixation device of claim 20, wherein by rotating the drive member a second distance, the drive member moves the second gripper toward the proximal end of the device without further pivoting the bendable member of the second gripper away from the longitudinal axis.

22. The bone fixation device of claim 21, wherein the first gripper and the second gripper are drawn toward one another, thereby approximating a fracture in a bone.

23. The bone fixation device of claim 18 wherein each of the bendable members extends toward the distal end of the elongate body.

24. The bone fixation device of claim 18 wherein the flexible-to-rigid portion of the elongate body is disposed at a location on the elongate body distal to both the first and second grippers.

25. The bone fixation device of claim 24, the elongate body further comprising a drive member positioned proximally to the flexible-to-rigid portion of the elongate body and threadably engaged with the actuator.

26. The bone fixation device of claim 18 wherein the flexible-to-rigid portion of the elongate body is disposed at a location on the elongate body proximal to the first gripper and distal to the second gripper.

* * * * *

UNITED STATES PATENT AND TRADEMARK OFFICE
CERTIFICATE OF CORRECTION

| | | |
|---|---|---|
| PATENT NO. | : 8,287,539 B2 | Page 1 of 1 |
| APPLICATION NO. | : 12/482388 | |
| DATED | : October 16, 2012 | |
| INVENTOR(S) | : Nelson et al. | |

It is certified that error appears in the above-identified patent and that said Letters Patent is hereby corrected as shown below:

Title Page, (item 75 Inventors) at line 4-5, Change "Santa Rosa, CA" for Heber Saravia to --San Francisco, CA--.

In column 2 at line 61, Change "and or" to --and/or--.

In column 3 at line 24, Change "U.S. Pat. No. U.S. Pat. No." to --U.S. Pat. No.--.

In column 4 at line 36, Change "huberus," to --humerus,--.

In column 10 at line 37, Change "supracondular," to --supracondylar,--.

In column 10 at line 38, Change "condular" to --condylar--.

In column 10 at line 58, Change "and or" to --and/or--.

In column 10 at line 59, Change "and or" to --and/or--.

In column 17 at line 34, Change "canulated" to --cannulated--.

In column 18 at line 8, Change "bracheoplexus)" to --brachial plexus)--.

In column 20 at line 9, Change "canulated" to --cannulated--.

In column 20 at line 22-23, Change "of the of the" to --of the--.

In column 22 at line 53, Change "canulated" to --cannulated--.

In column 23 at line 47, Change "malleoulus" to --malleolus--.

In column 23 at line 49, Change "themetatarsus;" to --the metatarsus;--.

Signed and Sealed this
Second Day of April, 2013

Teresa Stanek Rea
*Acting Director of the United States Patent and Trademark Office*